US008183037B2

(12) United States Patent
Wang

(10) Patent No.: US 8,183,037 B2
(45) Date of Patent: May 22, 2012

(54) METHODS OF GENETICALLY ENCODING UNNATURAL AMINO ACIDS IN EUKARYOTIC CELLS USING ORTHOGONAL TRNA/SYNTHETASE PAIRS

(75) Inventor: Lei Wang, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 1058 days.

(21) Appl. No.: 12/098,395

(22) Filed: Apr. 4, 2008

(65) Prior Publication Data

US 2008/0254540 A1 Oct. 16, 2008

Related U.S. Application Data

(60) Provisional application No. 60/923,247, filed on Apr. 13, 2007.

(51) Int. Cl.
C12N 15/79 (2006.01)
C12N 15/64 (2006.01)
C12N 5/10 (2006.01)
(52) U.S. Cl. .................... 435/320.1; 435/325; 435/455
(58) Field of Classification Search .................. None
See application file for complete search history.

(56) References Cited

U.S. PATENT DOCUMENTS

| | | | | |
|---|---|---|---|---|
| 6,071,700 | A * | 6/2000 | He et al. ............................. | 435/6 |
| 7,354,761 | B2 * | 4/2008 | Schultz et al. ................. | 435/325 |
| 7,368,275 | B2 * | 5/2008 | Schultz et al. .............. | 435/252.3 |
| 2003/0144239 | A1 * | 7/2003 | Agami et al. .................... | 514/44 |
| 2004/0265952 | A1 | 12/2004 | Deiters et al. | |
| 2005/0136513 | A1 | 6/2005 | Zhang et al. | |
| 2006/0134748 | A1 * | 6/2006 | RajBhandary et al. ...... | 435/69.1 |
| 2008/0254540 | A1 | 10/2008 | Wang | |

FOREIGN PATENT DOCUMENTS

WO WO 03/033521 A1 4/2003

OTHER PUBLICATIONS

Neu-Yilik et al. (2004) Genome Biology, vol. 5, 218-221.*
Monahan, "Natural and Unnatural Amino Acid Incorporation into Ion Channels Expressed in Mammalian Cells by Nonsense Suppression," Internet Citation, http://etd.caltech.edu/etd/available/etd-05252004-153512/unrestricted, pp. 96-128, 2004.
Monahan, "Site-Specific Incorporation of Unnatural Amino Acids into Receptors Expressed in Mammalian Cells," Internet Citation, http://resolver.caltech.edu/CaltechETD:etd-05252004-153512, Thesis, 146 pages, 2004.
Köhrer et al., "Import of amber and ochre suppressor tRNAs into mammalian cells: A general approach to site-specific insertion of amino acid analogues into proteins," PNAS, vol. 98, No. 25, pp. 14310-14315, 2001.
Köhrer et al., "A Possible Approach to Site-Specific Insertion of Two Different Unnatural Amino Acids into Protein in Mammalian Cells via Nonsense Suppression," Chemistry and Biology, vol. 10, pp. 1095-1102, 2003.
Folk et al., "Some Bacterial tRNA genes are transcribed by eukaryotic RNA polymerase III," Nucleic Acids Research, vol. 10, No. 22, pp. 7153-7162, 1982.
Edwards et al., "A bacterial amber suppressor in Saccharomyces cerevisiae is selectively recognized by a bacterial aminoacyl-tRNA synthetase,"Molecular and Cellular Biology, vol. 10, No. 4, pp. 1633-1641, 1990.
Chin et al., "Progress Toward an Expanded Eukaryotic Genetic Code," Chemistry & Biology, 10:511-519 (2003).
Hausmann et al., "The unnatural culture of amino acids," Nature Methods, 4(3):205-206 (2007).
Hino et al., "Protein photo-cross-linking in mammalian cells by site-specific incorporation of a photoreactive amino acid," Nature Methods, 2(3):201-206 (2005).
Köhrer et al., "Complete set of orthogonal 21$^{st}$ aminoacyl-tRNA synthetase-amber, ochre and opal suppressor tRNA pairs: concomitant suppression of three different termination codons in an mRNA in mammalian cells," Nucleic Acids Research, 32(21):6200-6211 (2004).
Liu et al., "Genetic incorporation of unnatural amino acids into proteins in mammalian cells," Nature Methods,4(3):239-244 (2007).
Paule & White, "Transcription by RNA polymerases I and III," Nucleic Acids Research, 28(6):1283-1298 (2000).
Parrish et al., "Manipulating Proteins for Neuroscience," Curr. Opin. Neurobiol. 16:585-592 (2006).
Ryu & Schultz, "Efficient incorporation of unnatural amino acids into proteins in Escherichia coli," Nature Methods, 3(4):263-265 (2006).
Sakamoto et al., "Site-specific incorporation of an unnatural amino acid into proteins in mammalian cells," Nucleic Acids Research, 30(21):4692-4699 (2002).
Wang & Schultz, "Expanding the Genetic Code," Angew. Chem. Int. Ed., 44:34-66 (2005).
Wang et al., "Expanding the Genetic Code," Annu. Rev. Biophys. Biomol. Struct. 35:225-249 (2006).
Wang & Tsien, "Evolving Proteins in Mammalian Cells Using Somatic Hypermutation," Nature Protocols 1(3):1346-1350 (2006).
Wang et al., "Genetically Encoding Unnatural Amino Acids for Cellular and Neuronal Studies," Nat. Neurosci., 10(8):1063-1072 (2007).

(Continued)

Primary Examiner — Anne Marie S Wehbe
(74) Attorney, Agent, or Firm — Kilpatrick Townsend & Stockton LLP

(57) ABSTRACT

This disclosure concerns compositions and methods for genetically encoding and expressing prokaryotic tRNAs in eukaryotic cells. In some embodiments, the disclosure concerns methods and compositions for expressing unnatural amino acids in eukaryotic cells using orthogonal tRNA/synthetase pairs. In certain embodiments, the methods involve expressing prokaryotic tRNA/synthetase pairs in eukaryotic cells, for instance mammalian cells or yeast cells (such as those that are NMD-deficient), under the control of a pol III promoter, for instance a type-3 pol III promoter or an internal leader promoter. Also provided are cell lines that are NMD-deficient and methods of increasing the efficiency of UAA incorporation in a cell that include de-activating the NMD pathway in the cell. Also provided are methods increasing the efficiency of incorporation of an unnatural amino acid in a cell by disrupting a Nonsense-Mediated mRNA Decay—(NMD) pathway in the cell.

28 Claims, 7 Drawing Sheets

OTHER PUBLICATIONS

Wang & Wang, "New Methods Enabling Efficient Incorporation of Unnatural Amino Acids in Yeast," *J. Am. Chem. Soc.*, 130(19):6066-6067 (2008).

Willis, "RNA polymerase III: Genes, factors and transcriptional specificity," *Eur. J. Biochem.*, 212:1-11 (1993).

Zhang et al., "Selective incorporation of 5-hydroxytryptophan into proteins in mammalian cells," *PNAS*, 101(24):8882-8887 (2004).

International Search Report from related PCT/US2008/59502 application (2008).

Written Opinion dated Jun. 27, 2008 from related PCT/US2008/59502 application (2008).

"22-Amino Acid Bacterium Created by Scientists at The Scripps Research Institute," Press Release, The Scripps Research Institute, May 11, 2004.

Kobayashi et al., "Structural Basis for Orthogonal tRNA Specificities of Tyrosyl-tRNA Synthetases for Genetic Code Expansion," *Nature Struct. Biol.* 10:425-432, 2003.

Perna et al., "Genome Sequence of Enterohaemorrhagic *Escherichia coli* O157:H7," GenBank Direction Submission, Accession F85770, Sep. 2001.

* cited by examiner

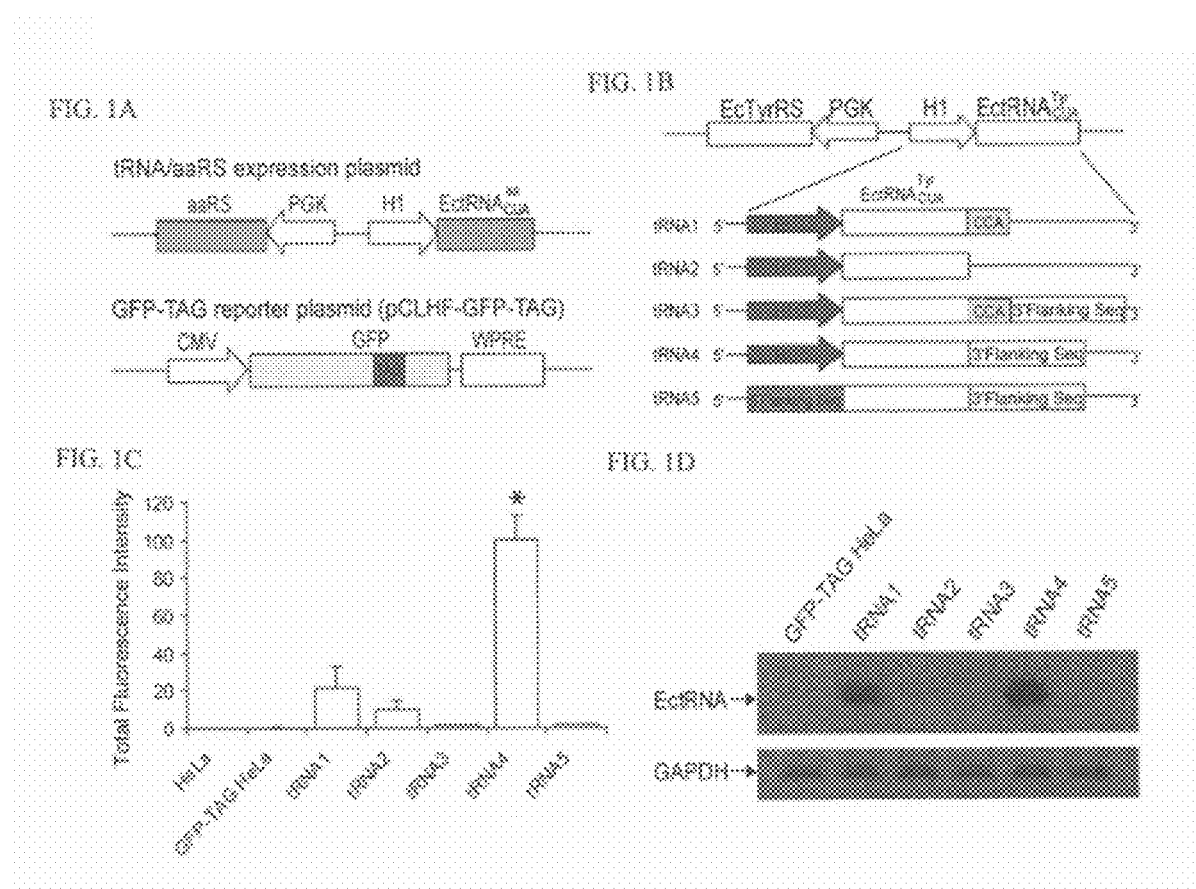

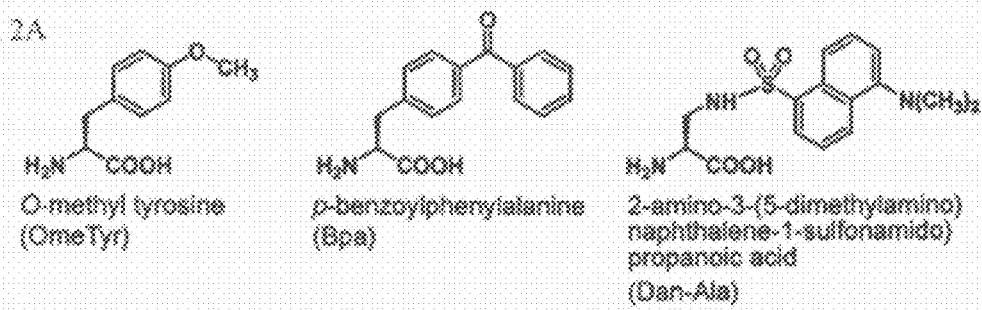
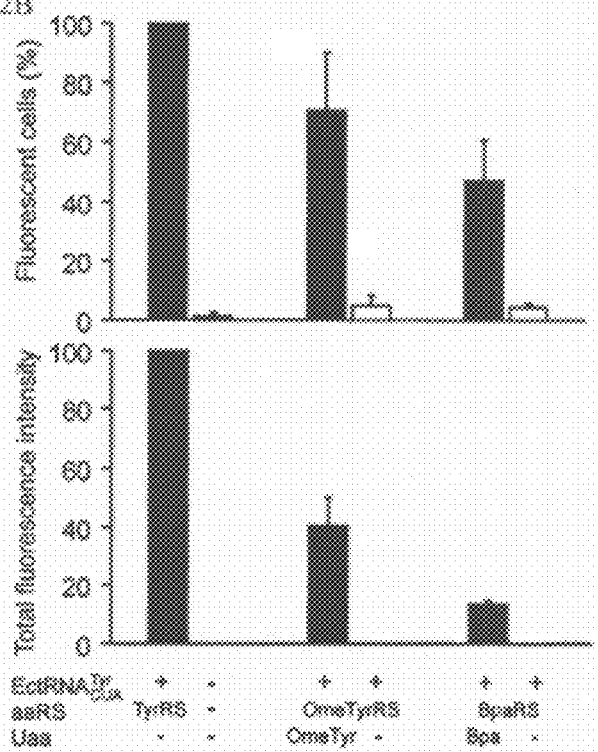
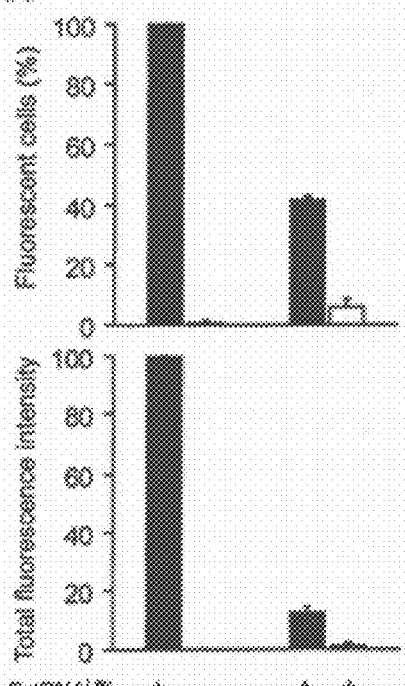

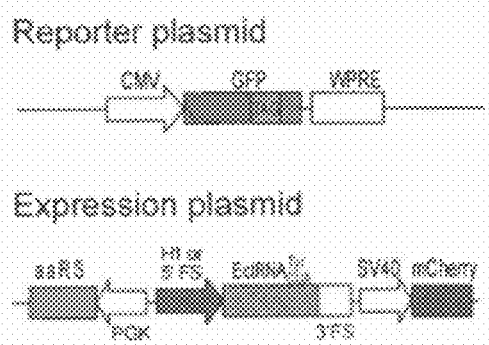
FIG. 3A
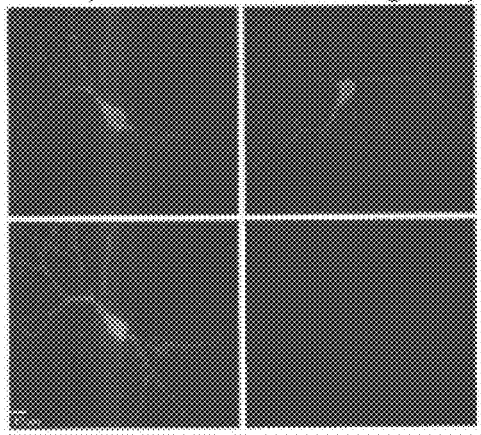
FIG. 3B EctRNA$^{Tyr}_{CUA}$/EcTyrRS
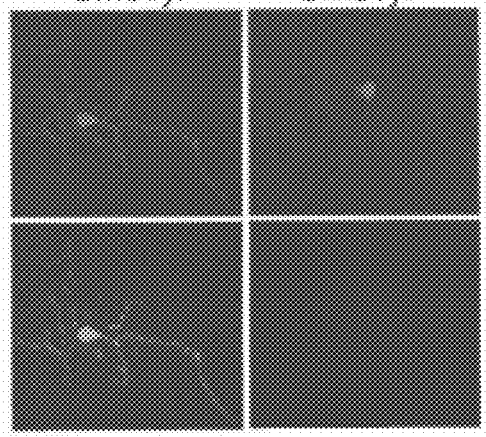
FIG. 3C EctRNA$^{Tyr}_{CUA}$/Ome-TyrRS
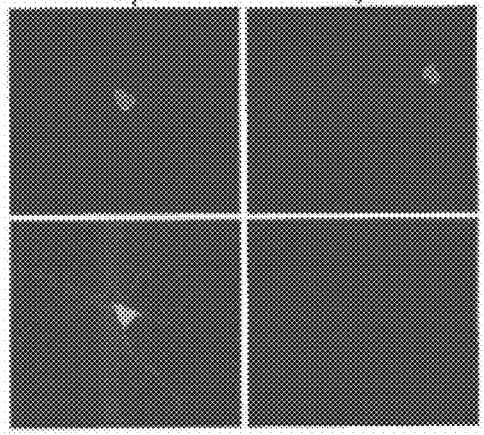
FIG. 3D EctRNA$^{Tyr}_{CUA}$/BpaRS

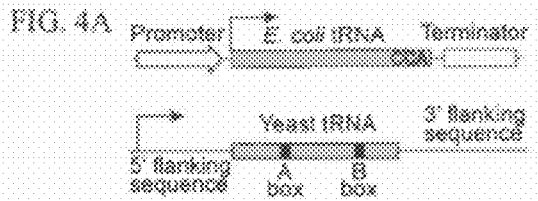
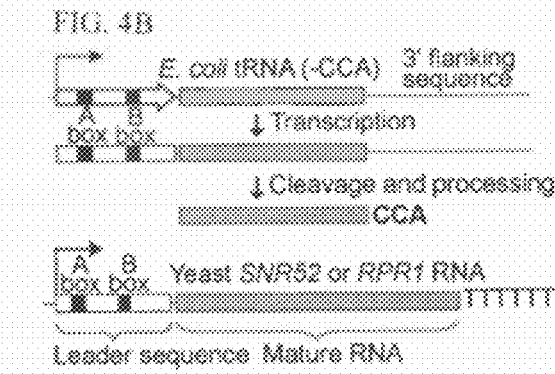
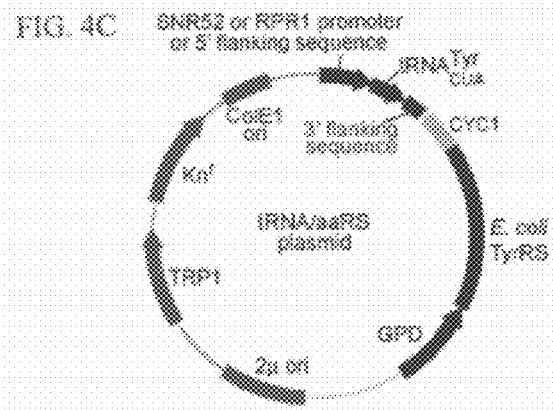
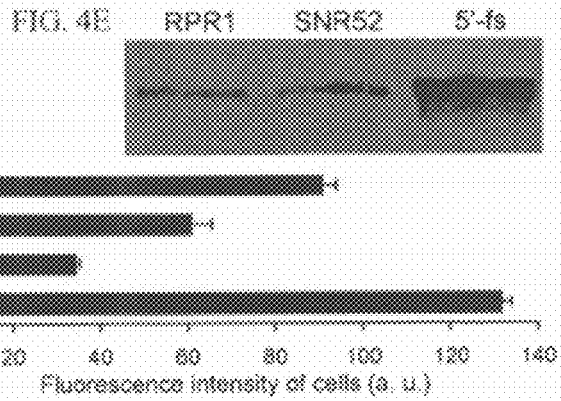

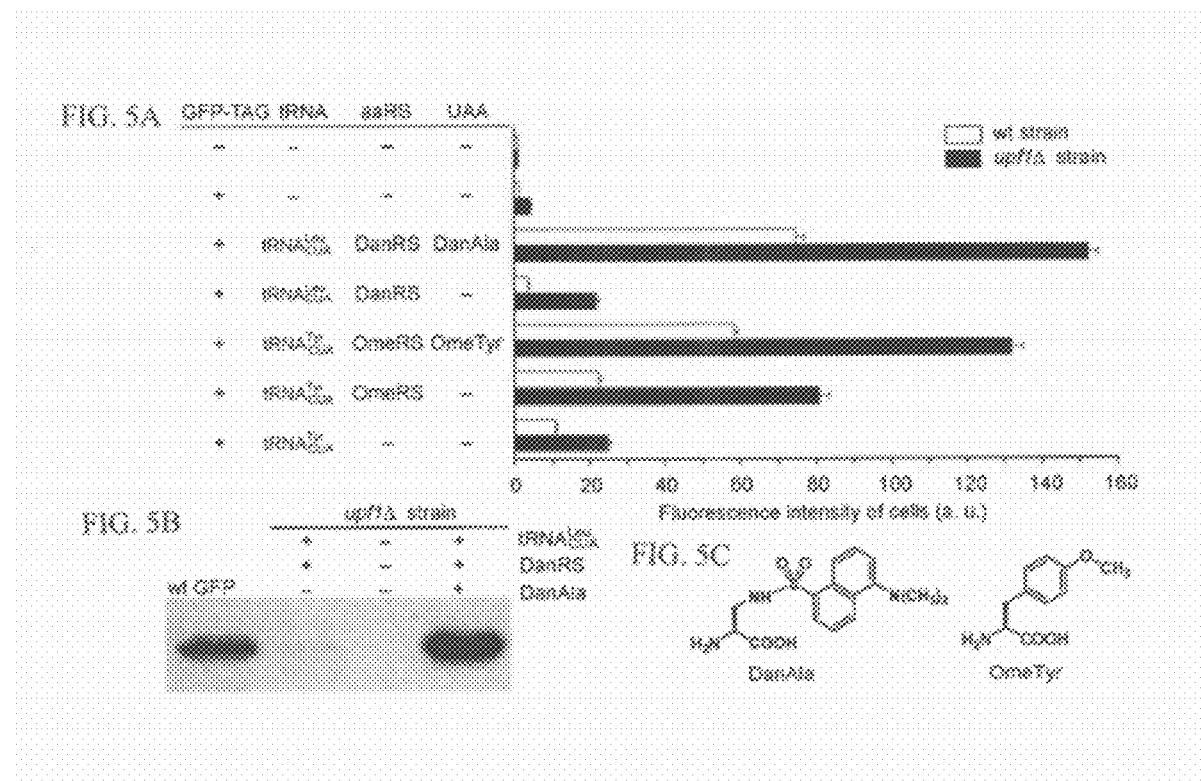

US 8,183,037 B2

METHODS OF GENETICALLY ENCODING UNNATURAL AMINO ACIDS IN EUKARYOTIC CELLS USING ORTHOGONAL TRNA/SYNTHETASE PAIRS

CROSS REFERENCE TO RELATED APPLICATION

This application claims of the filing date of U.S. Provisional Application No. 60/923,247, filed Apr. 13, 2007, the disclosure of which is incorporated herein in its entirety.

FIELD OF THE DISCLOSURE

This disclosure concerns compositions and methods for genetically encoding and expressing prokaryotic tRNAs in eukaryotic cells. In certain embodiments, the disclosure concerns methods and compositions for expressing unnatural amino acids in eukaryotic cells using orthogonal tRNA/synthetase pairs.

BACKGROUND

The incorporation of unnatural chemical groups into proteins has increasing importance in protein science and cell biology, and the biosynthesis of proteins containing unnatural amino acids can expand the structural and chemical diversity in proteins. One method of incorporating unnatural amino acids into proteins includes microinjecting chemically acylated tRNA and UAG-containing mutant mRNA into cells. Unfortunately, because this method involves microinjection, the technique is limited mainly to large *Xenopus* oocytes, and it is not suitable for studies that require large numbers of cells. Moreover, the tRNA is chemically acylated with the unnatural amino acid in vitro, and the acylated tRNA is consumed as a stoichiometric reagent during translation and cannot be regenerated. Therefore, yields of mutant proteins are low and long periods of data collection are not feasible.

Genetically encoding unnatural amino acids in cells can be used to study proteins in their native environment within the cell. One such method for expanding the genetic code to include unnatural amino acids was developed in *E. coli* (Wang et al., (2001) *Science* 292, 498-500). This method involved the generation of a new tRNA/aminoacyl-tRNA synthetase pair that was specific for an unnatural amino acid, and that decoded a blank codon unused by a common amino acid (such as a stop codon or extended codon). The tRNA/synthetase pair worked with the protein biosynthesis machinery of the host cell, and did not crosstalk with endogenous multiple tRNA/synthetase pairs.

However, genetically encoding unnatural amino acids in eukaryotes is more complicated because eukaryotic cells (including mammalian cells) and *E. coli* differ significantly in tRNA transcription, processing and transportation, leading to inefficient biosynthesis of orthogonal prokaryotic tRNAs in mammalian cells. If it were possible to genetically encode unnatural amino acids in eukaryotic cells, for instance yeast or mammalian cells, such a method would be a powerful tool in fields such as protein science, neuroscience, and cell biology.

SUMMARY OF THE DISCLOSURE

Disclosed herein are methods of expressing a prokaryotic tRNA in a eukaryotic cell that take advantage of the discovery that pol III promoters can be exploited to efficiently express and process prokaryotic tRNAs in eukaryotic cells. In particular examples, these methods include transducing a eukaryotic cell with a nucleic acid molecule that encodes a pol III promoter and a nucleic acid molecule that encodes a prokaryotic tRNA, thereby expressing the prokaryotic tRNA in the eukaryotic cell. In some embodiments, the methods include further transducing the eukaryotic cell with a nucleic acid molecule that encodes an aminoacyl-tRNA synthetase. In a specific example, a eukaryotic cell is transformed with an aminoacyl-tRNA synthetase that is specific for an unnatural amino acid, thereby permitting expression of the unnatural amino acid in the eukaryotic cell. In a specific example, the cell is a yeast cell or a mammalian cell that is substantially Nonsense-Mediated mRNA Decay—(NMD)-deficient.

Also disclosed are kits for carrying out the methods described above. In some embodiments, these kits include a plasmid that includes a nucleic acid molecule that encodes a pol III promoter, and a nucleic acid molecule that encodes a prokaryotic tRNA. In some examples, the plasmid further includes a nucleic acid molecule that encodes an aminoacyl-tRNA synthetase.

Stable eukaryotic cell lines also are provided that express a pol III promoter and a prokaryotic tRNA. In certain examples, the cells also express an exogenous aminoacyl-tRNA synthetase. In some examples the cell is NMD-deficient.

Also disclosed is a method for increasing the efficiency of incorporation of an unnatural amino acid in a cell which method includes disrupting a Nonsense-Mediated mRNA Decay—(NMD) pathway in the cell The foregoing and other features will become more apparent from the following detailed description of several embodiments, which proceeds with reference to the accompanying figures.

BRIEF DESCRIPTION OF THE FIGURES

FIG. 1 includes several panels demonstrating efficient expression of prokaryotic tRNA in mammalian cells using an H1 promoter. FIG. 1A is a schematic diagram of the expression plasmid and the reporter plasmid used in a fluorescence-based assay for the expression of functional tRNA in mammalian cells. The candidate amber suppressor tRNA and its cognate synthetase were expressed using the tRNA/aaRS expression plasmid. A reporter plasmid was used to express green fluorescent protein (GFP) with an amber stop codon at a permissive site. FIG. 1B is a schematic illustration of several tRNA/aaRS expression plasmids that use different elements to drive tRNA transcription and processing. FIG. 1C is a graph showing the total fluorescence intensity of the fluorescent GFP-TAG in HeLa cells after transfection with the constructs shown in FIG. 1B. The intensities were normalized to those of cells transfected with tRNA4. The values (±SD) were: GFP-TAG HeLa 0.3±0.1, tRNA1 21±11, tRNA2 10±4.7, tRNA3 1.3±0.7, tRNA4 100±12, tRNA5 1.4±0.5. For all samples, n=5. FIG. 1D is a digital image of a Northern blot analysis showing the amount of transcribed $EctRNA_{CUA}^{Tyr}$ in HeLa cells. Transcript of glyceraldehyde-3-phosphate dehydrogenase (GAPDH) was used to normalize the total amount of RNA in different samples.

FIG. 2 includes several panels demonstrating that unnatural-amino-acid specific synthetases evolved in yeast are functional in mammalian cells. FIG. 2A shows the chemical structures of the three unnatural amino acids used. FIG. 2B is a pair of graphs showing incorporation of OmeTyr and Bpa into GFP in the GFP-TAG HeLa cells using the $EctRNA_{CUA}^{Tyr}$ and corresponding synthetases evolved from *E. coli* TyrRS in yeast. All data were normalized to those obtained from GFP-TAG HeLa cells transfected with the $EctRNA_{CUA}^{Tyr}$ and wt *E.*

*coli* TyrRS. The percentages of fluorescent cells were: 71±19 (+OmeTyr, n=3), 4.8±3.4 (−OmeTyr, n=3), 47±14 (+Bpa, n=3), and 4.2±1.5 (−Bpa, n=3). The total fluorescence intensities were: 41±9.5 (+OmeTyr, n=3), 0.17±0.02 (−OmeTyr, n=3), 13±1.4 (+Bpa, n=3), and 0.11±0.06 (−Bpa, n=3). FIG. 2C is a pair of graphs showing incorporation of Dan-Ala into GFP in the GFP-TAG HeLa cells using the EctRNA$_{CUA}^{Leu}$ and a Dan-Ala specific synthetase evolved from *E. coli* LeuRS. The data in these figures were normalized as in FIG. 2B. The percentages of fluorescent cells were: 42±1.3 (+DanAla, n=3) and 5.9±2.6 (−DanAla, n=3). The total fluorescence intensities were: 13±2.1 (+DanAla, n=3) and 1.4±1.0 (−DanAla, n=3).

FIG. 3 includes several panels demonstrating that unnatural amino acids can be genetically encoded in neurons. FIG. 3A is a schematic illustration of the reporter plasmid expressing the GFP mutant gene with a TAG stop codon at site 182 and the expression plasmid encoding the EctRNA$_{CUA}^{Tyr}$, the synthetase, and an internal transfection marker mCherry. FIG. 3B includes four digital fluorescence images of neurons transfected with the reporter plasmid, the EctRNA$_{CUA}^{Tyr}$, and wt *E. coli* TyrRS. The tRNA expression was driven by the H1 promoter in the left panels, and by the 5' flanking sequence of the human tRNA$^{Tyr}$ in the right panels. FIG. 3C includes four digital fluorescence images of neurons transfected with the reporter plasmid, the ECtRNA$_{CUA}^{Tyr}$, and the OmeTyrRS in the presence (left panels) and absence (right panels) of OmeTyr. FIG. 3D includes four digital fluorescence images of neurons transfected with the reporter plasmid, the ECtRNA$_{CUA}^{Tyr}$, and the BpaRS in the presence (left panels) and absence (right panels) of Bpa.

FIG. 4 includes several panels demonstrating a method for enhancing the efficiency of expression of *E. coli* tRNAs in yeast. FIG. 4A is a schematic diagram showing the gene elements for tRNA transcription in *E. coli* and in yeast. FIG. 4B is a schematic diagram showing an enhanced method for expressing *E. coli* tRNAs in yeast using a Pol III promoter that contains the conserved A- and B-box and that is cleaved from the primary transcript. Gene organization of yeast SNR52 or RPR1 RNA is shown at the bottom. FIG. 4C is a schematic diagram showing the plasmids encoding the orthogonal EctRNA$_{CUA}^{Tyr}$/TyrRS pair and the GFP-TAG reporter, respectively. FIG. 4D is a chart showing the fluorescence assay results for the functional expression of EctRNA$_{CUA}^{Tyr}$ and EctRNA$_{CUA}^{Tyr}$ driven by different promoters in yeast. Error bars represent s.e.m. n=3. FIG. 4E is a digital image of a gel showing a Northern analysis of ECtRNA$_{CUA}^{Tyr}$ expressed in yeast by the indicated promoters.

FIG. 5 includes three panels showing that NMD inactivation increases the incorporation efficiency of UAAs in yeast. FIG. 5A is a graph showing the fluorescence assay results for UAA incorporation in wt and the upf1 Δ strain. Error bars represent s.e.m. n=3. FIG. 5B is a digital image of a gel showing a Western analysis of the DanAla-containing GFP expressed in the upf1Δ strain. The same amounts of cell lysate from each sample were separated by SDS-PAGE and probed with an anti-His5 antibody. FIG. 5C shows the UAA structures of Dan/Ala and OmeTyr.

FIG. 6 includes two panels showing incorporation of UAAs into GFP using the H1 promoter in stem cells.

FIG. 7 includes two panels showing incorporation of two UAAs, p-benzoylphenylalanine and dansylalanine, using the H1 promoter in stem cells.

SEQUENCE LISTING

Figure 6A:
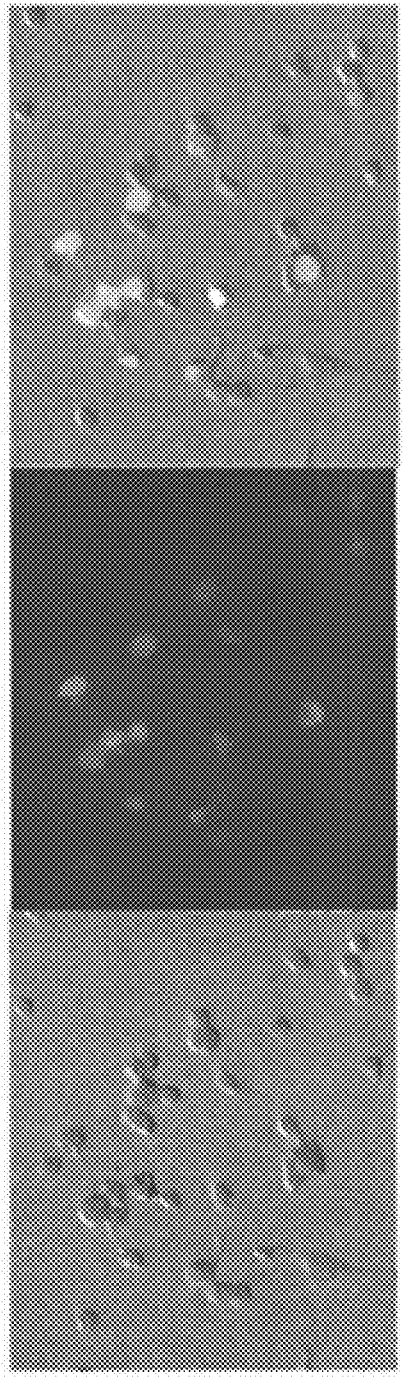
FIG. 6A shows that the H1 promoter can express the orthogonal *E. coli* tRNA$^{Tyr}$ in HCN cells. Together with the orthogonal *E. coli* TyrRS, the tRNA$^{Tyr}$ incorporates Tyr into the GFP and makes the cells fluorescent.

The nucleic acid sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 show forward and reverse primer sequences, respectively, used to amplify the *E. coli* TyrRS gene.

SEQ ID NOs: 3 and 4 show forward and reverse primer sequences, respectively, used to amplify the gene for EctRNA$_{CUA}^{Tyr}$ in construct tRNA2.

SEQ ID NOs: 5 and 6 show forward and reverse primer sequences, respectively, used to amplify the gene for the *E. coli* LeuRS gene.

SEQ ID NOs: 7 and 8 show forward and reverse primer sequences, respectively, used to amplify the gene for $^{32}$P-labeled DNA probes specific for the ECtRNA$_{CUA}^{Tyr}$.

SEQ ID NOs: 9 and 10 show forward and reverse primer sequences FW19 and FW20, respectively, used to amplify a spacer sequence from pcDNA3.

SEQ ID NOs: 11 and 12 show forward and reverse primer sequences FW21 and FW22, respectively, used to amplify the *E. coli* TyrRS gene from *E. coli* genomic DNA.

SEQ ID NOs: 13 and 14 show forward and reverse primer sequences FW16 and FW17, respectively, used to amplify the SNR52 promoter from yeast genomic DNA.

SEQ ID NOs: 15 and 16 show forward and reverse primer sequences FW14 and FW15, respectively, used to amplify the EctRNA$_{CUA}^{Tyr}$ gene followed by the 3'-flanking sequence of the SUP4 suppressor tRNA from pEYCUA-YRS.

SEQ ID NOs: 17 and 18 show forward and reverse primer sequences FW12 and FW13, respectively, used to amplify the RPR1 promoter from yeast genomic DNA.

SEQ ID NO: 19 shows a forward primer sequence used to amplify a gene cassette containing the 5' flanking sequence of the SUP4 suppressor tRNA, the EctRNA$_{CUA}^{Tyr}$, and the 3' flanking sequence of the SUP4 suppressor tRNA from plasmid pEYCUA-YRS-tRNA-5.

SEQ ID NOs: 20 and 21 show forward and reverse primer sequences FW27 and FW28, respectively, used to amplify a gene cassette containing the 5' flanking sequence of the SUP4 suppressor tRNA, the EctRNA$_{CUA}^{Tyr}$, and the 3' flanking sequence of the SUP4 suppressor tRNA from plasmid pLeuRSB8T252A.

SEQ ID NOs: 22 and 23 show forward and reverse primer sequences FW29 and FW30, respectively, used to amplify the *E. coli* LeuRS gene from *E. coli* genomic DNA.

SEQ ID NO: 24 shows a reverse primer sequence FW31 used to amplify the SNR52 promoter from pSNR-TyrRS.

SEQ ID NO: 25 shows a forward primer sequence FW32 used to amplify the EctRNA$_{CUA}^{Leu}$-3' flanking sequence fragment from pLeuRSB8T252A.

SEQ ID NOs: 26 and 27 show forward and reverse primer sequences JT171 and JT172, respectively, used to amplify a mutant GFP-TAG gene.

SEQ ID NO: 28 shows the sequence of a biotinylated probe FW39 which is specific for the *E. coli* tRNA$^{Tyr}$ and the EctR-NA$_{CUA}^{Tyr}$.

SEQ ID NOs: 29 and 30 show forward and reverse primer sequences FW5 and FW6, respectively, used to amplify a gene cassette containing ~200 bp upstream of UPF1, the Kan-MX6, and ~200 bp downstream of UPF1.

SEQ ID NOs: 31 and 32 show forward and reverse primer sequences, respectively, used to amplify genomic DNA ~300 bp away from the UPF1 gene.

SEQ ID NO: 33 is the nucleic acid sequence encoding O-EctRNA$_{CUA}^{Tyr}$.

SEQ ID NO: 34 is the nucleic acid sequence encoding O-EctRNA$_{CUA}^{Tyr}$.

DETAILED DESCRIPTION

I. Overview of Several Embodiments

Disclosed herein are methods of expressing a prokaryotic tRNA in a eukaryotic cell that takes advantage of the surprising discovery that polymerase III promoters can be used to drive expression of prokaryotic tRNAs in eukaryotic cells. It was also surprisingly observed that in some eukaryotic cells, such as yeast and mammalian cells, inactivation of the Nonsense-Mediated mRNA Decay (NMD) pathway enhances incorporation efficiency of unnatural amino acids (UAAs). In one embodiment, the method involves transducing a eukaryotic cell with a nucleic acid molecule encoding an external RNA polymerase III promoter (pol III) operably linked to a nucleic acid molecule encoding the prokaryotic tRNA, thereby expressing the prokaryotic tRNA in the eukaryotic cell. In some examples, the eukaryotic cell is a mammalian cell, and in more particular examples, the cell is a neuron, or an isolated human cell.

Further embodiments of the method include the additional step of transducing the eukaryotic cell with a nucleic acid molecule that encodes an aminoacyl-tRNA synthetase operably linked to a promoter. In some examples, the aminoacyl-tRNA synthetase is specific for an unnatural amino acid (UAA), and the method is a method of co-expressing the prokaryotic tRNA and the unnatural amino acid. In certain examples, the tRNA and the aminoacyl-tRNA synthetase form an orthogonal pair.

Other embodiments are methods for increasing the efficiency of incorporation of an unnatural amino acid in a cell, which method includes disrupting a Nonsense-Mediated mRNA Decay—(NMD) pathway in the cell. Also disclosed are cells that are substantially NMD-deficient.

Also disclosed herein are kits that contain a vector that includes a nucleic acid molecule encoding a pol III promoter operably linked to a nucleic acid molecule that encodes a prokaryotic tRNA. In particular examples, the pol III promoter is an internal leader promoter, such as the SNR52 promoter or the RPR1 promoter. In some examples, the vector is an expression plasmid.

Some embodiments of the kit also contain a nucleic acid molecule that encodes an aminoacyl-tRNA synthetase, and in certain examples, the aminoacyl-tRNA synthetase is specific for a UAA. In particular examples, the tRNA and the aminoacyl-tRNA synthetase form an orthogonal pair.

Also disclosed are stable eukaryotic cells expressing a nucleic acid molecule encoding a pol III promoter operably linked to a prokaryotic tRNA, which cells are, in some examples, deficient in the NMD pathway. Also provided are cells, such as mammalian cells, that have a deficient or inactive NMD pathway. In some embodiments, the cells are a cell line, such as a mammalian cell line, and in particular examples, the mammalian cell line is a human cell line. In one specific example, the cell is a yeast cell that is deficient NMD pathway. In another example, the cell is a neuron, such as a human neuron. In some examples, the cell is a stem cell.

Some embodiments of the cell line also express an aminoacyl-tRNA synthetase, and in certain examples, the tRNA and the aminoacyl-tRNA synthetase form an orthogonal pair. In still other embodiments, the aminoacyl-tRNA synthetase is specific for an unnatural amino acid. The pol III promoter, in some embodiments, is a type-3 pol III promoter, and in certain examples, the type-3 pol III promoter is a promoter that is itself not transcribed but instead has a defined starting transcription site for direct tRNA transcription. In other examples, the pol III promoter is an internal leader promoter that is transcribed together with the tRNA, and is then cleaved post-transcriptionally to yield the tRNA, such as the SNR52 promoter or the RPR1 promoter. In some embodiments, the prokaryotic tRNA is an *E. coli* tRNA, and in certain examples, the prokaryotic tRNA is a suppressor tRNA, for instance an amber, ochre, opal, missense, or frameshift tRNA. In particular examples, the suppressor tRNA is *E. coli* tyrosyl amber tRNA. In more particular examples, the tRNA decodes a stop codon or an extended codon.

The UAA can include, in some embodiments, a detectable label such as a fluorescent group, a photoaffinity label, or a photo-caged group, a crosslinking agent, a polymer, a cytotoxic molecule, a saccharide, a heavy metal-binding element, a spin label, a heavy atom, a redox group, an infrared probe, a keto group, an azide group, or an alkyne group. In some embodiments, the UAA is a hydrophobic amino acid, a β-amino acid, a homo-amino acid, a cyclic amino acid, an aromatic amino acid, a proline derivative, a pyruvate derivative, a lysine derivative, a tyrosine derivative, a 3-substituted alanine derivative, a glycine derivative, a ring-substituted phenylalanine derivative, a linear core amino acid, or a diamino acid. In particular embodiments of the method, the nucleic acid encoding the pol III operably linked to the nucleic acid encoding the prokaryotic tRNA further includes either a 3'-CCA trinucleotide at a 3'-end of the nucleic acid encoding the bacterial tRNA or a 3' flanking nucleic acid sequence at the 3' end of the nucleic acid encoding the bacterial tRNA.

II. Abbreviations

| | |
|---|---|
| ADH | alcohol dehydrogenase |
| BAC | bacterial artificial chromosome |
| BPA | p-benzoylphenylalanine |
| CAT | chloramphenicol acetyltransferase |
| DMEM | Dulbecco's modified Eagle's medium |
| DNA | deoxyribonucleic acid |
| EctRNA$_{CUA}^{aa}$ | *E. coli* amber suppressor tRNA, anticodon CUA |
| EDTA | ethylenediaminetetraacetic acid |
| EGFP | enhanced green fluorescent protein |
| GAPDH | glyceraldehyde-3-phosphate dehydrogenase |
| GFP | green fluorescent protein |
| Leucyl-O-RS | orthogonal leucyl tRNA synthetase |
| LeuRS | leucyl tRNA synthetase |
| MCS | multiple cloning sites |
| NMD | Nonsense-Mediated mRNA Decay |
| O-RS | orthogonal aminoacyl-tRNA synthetase |
| O-tRNA | orthogonal tRNA |

| | |
|---|---|
| PAGE | polyacrylamide gel electrophoresis |
| PBS | phosphate buffered saline |
| PCR | polymerase chain reaction |
| Pol | polymerase |
| RNA | ribonucleic acid |
| RS | aminoacyl-tRNA synthetase |
| SDS | sodium dodecylsulfate |
| Tyrosyl-O-RS | orthogonal tyrosyl amino acid synthetase |
| TyrRS | tyrosyl amino acid synthetase |
| UAA | unnatural amino acid |
| WPRE | woodchuck hepatitis virus posttranscriptional regulatory element |
| Wt | wild-type |
| YAC | yeast artificial chromosome |

III. Terms

In order to facilitate review of the various embodiments of the disclosure, the following explanations of specific terms are provided:

Bacteria: Unicellular microorganisms belonging to the Kingdom Procarya. Unlike eukaryotic cells, bacterial cells do not contain a nucleus and rarely harbour membrane-bound organelles. As used herein, both Archaea and Eubacteria are encompassed by the terms "prokaryote" and "bacteria." Examples of Eubacteria include, but are not limited to *Escherichia coli*, *Thennus thermophilus* and *Bacillus stearothennophilus*. Example of Archaea include *Methanococcus jannaschii*, *Methanosarcina mazei*, *Methanobacterium thermoautotrophicum*, *Methanococcus maripaludis*, *Methanopyrus kandleri*, *Halobacterium* such as *Haloferax volcanii* and *Halobacterium* species NRC-i, *Archaeoglobus fulgidus*, *Pyrococcusfit riosus*, *Pyrococcus horikoshii*, *Pyrobaculum aerophilum*, *Pyrococcus abyssi*, *Sulfolobus solfataricus*, *Sulfolobus tokodaii*, *Aeuropyrum pernix*, *Thermoplasma acidophilum*, and *Thermoplasma volcanium*.

Conservative variant: As used herein, the term "conservative variant," in the context of a translation component, refers to a peptide or amino acid sequence that deviates from another amino acid sequence only in the substitution of one or several amino acids for amino acids having similar biochemical properties (so-called conservative substitutions). Conservative amino acid substitutions are likely to have minimal impact on the activity of the resultant protein. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. In some examples, O—RS variants can have no more than 3, 5, 10, 15, 20, 25, 30, 40, or 50 conservative amino acid changes. Conservative variants are discussed in greater detail in section IV K of the Detailed Description.

In one example, a conservative variant orthogonal tRNA (O-tRNA) or a conservative variant orthogonal aminoacyl-tRNA synthetase (O—RS) is one that functionally performs substantially like a similar base component, for instance, an O-tRNA or O—RS having variations in the sequence as compared to a reference O-tRNA or O—RS. For example, an O—RS, or a conservative variant of that O—RS, will aminoacylate a cognate O-tRNA with an unnatural amino acid, for instance, an amino acid including an N-acetylgalactosamine moiety. In this example, the O—RS and the conservative variant O—RS do not have the same amino acid sequence. The conservative variant can have, for instance, one variation, two variations, three variations, four variations, or five or more variations in sequence, as long as the conservative variant is still complementary to the corresponding O-tRNA or O—RS.

In some embodiments, a conservative variant O—RS includes one or more conservative amino acid substitutions compared to the O—RS from which it was derived, and yet retains O—RS biological activity. For example, a conservative variant O—RS can retain at least 10% of the biological activity of the parent O—RS molecule from which it was derived, or alternatively, at least 20%, at least 30%, or at least 40%. In some embodiments, a conservative variant O—RS retains at least 50% of the biological activity of the parent O—RS molecule from which it was derived. The conservative amino acid substitutions of a conservative variant O—RS can occur in any domain of the O—RS, including the amino acid binding pocket.

Encode: As used herein, the term "encode" refers to any process whereby the information in a polymeric macromolecule or sequence is used to direct the production of a second molecule or sequence that is different from the first molecule or sequence. As used herein, the term is construed broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (for instance, by the process of transcription incorporating a DNA-dependent RNA polymerase enzyme). Also, an RNA molecule can encode a peptide, as in the process of translation. When used to describe the process of translation, the term "encode" also extends to the triplet codon that encodes an amino acid. In some aspects, an RNA molecule can encode a DNA molecule, for instance, by the process of reverse transcription incorporating an RNA-dependent DNA polymerase. In another aspect, a DNA molecule can encode a peptide, where it is understood that "encode" as used in that case incorporates both the processes of transcription and translation.

Eukaryote: Organisms belonging to the Kingdom Eucarya. Eukaryotes are generally distinguishable from prokaryotes by their typically multicellular organization (but not exclusively multicellular, for example, yeast), the presence of a membrane-bound nucleus and other membrane-bound organelles, linear genetic material (for instance, linear chromosomes), the absence of operons, the presence of introns, message capping and poly-A mRNA, and other biochemical characteristics known in the art, such as a distinguishing ribosomal structure. Eukaryotic organisms include, for example, animals (for instance, mammals, insects, reptiles, birds, etc.), ciliates, plants (for instance, monocots, dicots, algae, etc.), fungi, yeasts, flagellates, microsporidia, and protists. A eukaryotic cell is one from a eukaryotic organism, for instance a human cell or a yeast cell.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a cell, tissue or subject to an agent that increases or decreases gene expression. Expression of a gene also can be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression can be measured at the RNA level or the protein level and by any method known in the art, including, without limitation, Northern blot, RT-PCR, Western blot, or in vitro, in situ, or in vivo protein activity assay(s).

Hybridization: Oligonucleotides and their analogs hybridize to one another by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to an O—RS-encoding RNA, or an O-tRNA-encoding DNA.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

For purposes of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. Conditions for very high, high, and low stringency hybridization are discussed in greater detail below in section IVJ.

In particular embodiments, stringent conditions are hybridization at 65° C. in 6×SSC, 5×Denhardt's solution, 0.5% SDS and 100 μg sheared salmon testes DNA, followed by 15-30 minute sequential washes at 65° C. in 2×SSC, 0.5% SDS, followed by 1×SSC, 0.5% SDS and finally 0.2×SSC, 0.5% SDS.

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

Mammalian cell: A cell from a mammal, the class of vertebrate animals characterized by the production of milk in females for the nourishment of young, from mammary glands present on most species; the presence of hair or fur; specialized teeth; three small bones within the ear; the presence of a neocortex region in the brain; and endothermic or "warmblooded" bodies, and, in most cases, the existence of a placenta in the ontogeny. The brain regulates endothermic and circulatory systems, including a four-chambered heart. Mammals encompass approximately 5,800 species (including humans), distributed in about 1,200 genera, 152 families and up to forty-six orders, though this varies with the classification scheme.

Neurons: Electrically excitable cells in the nervous system that process and transmit information. In vertebrate animals, neurons are the core components of the brain, spinal cord and peripheral nerves. Neurons typically are composed of a soma, dendrites, and an axon. The majority of vertebrate neurons receive input on the cell body and dendritic tree, and transmit output via the axon. However, there is great heterogeneity throughout the nervous system and the animal kingdom, in the size, shape and function of neurons.

Neurons communicate via chemical and electrical synapses, in a process known as synaptic transmission. The fundamental process that triggers synaptic transmission is the action potential, a propagating electrical signal that is generated by exploiting the electrically excitable membrane of the neuron. Specific, non-limiting examples of vertebrate neurons include hippocampal neurons, cortical neurons, spinal neurons, motorneurons, sensory neurons, pyramidal neurons, cerebellar neurons, retinal neurons, and Purkinje cells.

Nonsense-Mediated mRNA Decay (NMD): A cellular mechanism of mRNA surveillance used by the cell to detect nonsense mutations and prevent the expression of truncated or erroneous proteins. NMD is triggered by exon-junction complexes that form during pre-RNA processing, being downstream of the nonsense codon. Normally, these exon-junction complexes are removed during the first round of translation of the mRNA, but in the case of a premature stop codon, they are still present on the mRNA. This is identified as a problem by NMD factors, and the RNA is degraded, for example by the exosome complex. A substantially Nonsense-Mediated mRNA Decay—(NMD)-deficient cell or cell line has little or no NMD activity, for instance less than 20%, 15%, 10%, 5%, 2%, 1%, or even less NMD activity as compared to a wild-type cell or cell line. Thus, an NMD-deficient cell or cell line degrades few or none of the mRNA premature stop codons that may be present in the cell, for instance a eukaryotic cell such as yeast cell or a mammalian cell.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules can be modified chemically or biochemically or can contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects the transcription or expression of the coding sequence. When recombinantly produced, operably linked nucleic acid sequences are generally contiguous and, where necessary to join two protein-coding regions, in the same reading frame. However, nucleic acids need not be contiguous to be operably linked.

Orthogonal: A molecule (for instance, an orthogonal tRNA (O-tRNA) and/or an orthogonal aminoacyl-tRNA synthetase (O—RS)) that functions with endogenous components of a cell with reduced efficiency as compared to a corresponding molecule that is endogenous to the cell, or that fails to function with endogenous components of the cell. In the context of tRNAs and aminoacyl-tRNA synthetases, orthogonal refers to an inability or reduced efficiency, for instance, less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA, such as 0-20% efficiency.

An orthogonal molecule lacks a functionally normal endogenous complementary molecule in the cell. For example, an orthogonal tRNA in a cell is aminoacylated by any endogenous aminoacyl-tRNA synthetase (RS) of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule.

Orthogonal tyrosyl-tRNA (O-tRNA): A tRNA that is orthogonal to a cell of interest, where the tRNA is: (1) identical or substantially similar to a naturally occurring leucyl or tyrosyl-tRNA, (2) derived from a naturally occurring leucyl or tyrosyl-tRNA by natural or artificial mutagenesis, (3) derived by any process that takes a sequence of a wild-type or mutant leucyl or tyrosyl-tRNA sequence of (1) or (2) into account, or (4) homologous to a wild-type or mutant leucyl or tyrosyl-tRNA. The leucyl or tyrosyl-tRNA can exist charged with an amino acid, or in an uncharged state. It is also to be understood that a "tyrosyl-O-tRNA" or "leucyl-O-tRNA" optionally is charged (aminoacylated) by a cognate synthetase with an amino acid other than tyrosine or leucine, respectively, for instance, with an unnatural amino acid. Indeed, it will be appreciated that a leucyl or tyrosyl-O-tRNA of the disclosure can be used to insert essentially any amino acid, whether natural or artificial, into a growing peptide, during translation, in response to a selector codon.

Orthogonal tyrosyl amino acid synthetase (O—RS): An enzyme that preferentially aminoacylates the tyrosyl-O-tRNA with an amino acid in a cell of interest. The amino acid that the tyrosyl-O—RS loads onto the tyrosyl-O-tRNA can be any amino acid, whether natural, unnatural or artificial, and is not limited herein.

Similarly, an orthogonal leucyl tRNA synthetase (Leucyl-O—RS) is an enzyme that preferentially aminoacylates the leucyl-O-tRNA with an amino acid in a cell of interest. The amino acid that the leucyl-O—RS loads onto the leucyl-O-tRNA can be any amino acid, whether natural, unnatural or artificial, and is not limited herein.

Plasmid: A DNA molecule separate from chromosomal DNA and capable of autonomous replication. It is typically circular and double-stranded, and can naturally occur in bacteria, and sometimes in eukaryotic organisms (for instance, the 2-micrometer-ring in *Saccharomyces cerevisiae*). The size of plasmids can vary from about 1 to over 400 kilobase pairs. Plasmids often contain genes or gene cassettes that confer a selective advantage to the bacterium (or other cell) harboring them, such as the ability to make the bacterium (or other cell) antibiotic resistant.

Plasmids contain at least one DNA sequence that serves as an origin of replication, which enables the plasmid DNA to be duplicated independently from the chromosomal DNA. The chromosomes of most bacteria are circular, but linear plasmids are also known.

Plasmids used in genetic engineering are referred to as vectors. They can be used to transfer genes from one organism to another, and typically contain a genetic marker conferring a phenotype that can be selected for or against. Most also contain a polylinker or multiple cloning site, which is a short region containing several commonly used restriction sites allowing the easy insertion of DNA fragments at this location. Specific, non-limiting examples of plasmids include pCLHF, pCLNCX (Imgenex), pCLHF-GFP-TAG, pSUPER (OligoEngine), pEYCUA-YRS, pBluescript II KS (Stratagene), pcDNA3 (Invitrogen).

Preferentially aminoacylates: As used herein in reference to orthogonal translation systems, an O—RS "preferentially aminoacylates" a cognate O-tRNA when the O—RS charges the O-tRNA with an amino acid more efficiently than it charges any endogenous tRNA in a cell. In particular examples, the relative ratio of O-tRNA charged by the O—RS to endogenous tRNA charged by the O—RS is high, resulting in the O—RS charging the O-tRNA exclusively, or nearly exclusively, when the O-tRNA and endogenous tRNA are present in equal molar concentrations in the translation system.

The O—RS "preferentially aminoacylates an O-tRNA with an unnatural amino acid" when (a) the O—RS preferentially aminoacylates the O-tRNA compared to an endogenous tRNA, and (b) where that aminoacylation is specific for the unnatural amino acid, as compared to aminoacylation of the O-tRNA by the O—RS with any natural amino acid. In specific examples, O—RS charges the O-tRNA exclusively, or nearly exclusively, with the unnatural amino acid.

Prokaryote: Organisms belonging to the Kingdom Monera (also termed Procarya). Prokaryotic organisms are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Promoter: A region of DNA that generally is located upstream (towards the 5' region of a gene) that is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene.

In prokaryotes, the promoter is recognized by RNA polymerase and an associated sigma factor, which in turn are brought to the promoter DNA by an activator protein binding to its own DNA sequence nearby. In eukaryotes, the process is more complicated. For instance, at least seven different factors are necessary for the transcription of an RNA polymerase II promoter. Promoters represent elements that can work in concert with other regulatory regions (enhancers, silencers, boundary elements/insulators) to direct the level of transcription of a given gene.

The promoters that are useful in carrying out the methods described herein include RNA polymerase III (also called Pol III) promoters, which transcribe DNA to synthesize ribosomal 5S rRNA, tRNA, and other small RNAs. Pol III is unusual (compared to Pol II) in that it requires no control sequences upstream of the gene. Instead, it can rely on internal control sequences. The RNA polymerase III promoters are more varied in structure than the uniform RNA polymerase I promoters, and yet not as diverse as the RNA polymerase II promoters. They have been divided into three main types (types 1-3), two of which are gene-internal and generally TATA-less, and one of which is gene-external and contains a TATA box.

Some embodiments of the described methods employ a type-3 promoter. Type-3 promoters were identified originally in mammalian U6 snRNA genes, which encode the U6 snRNA component of the spliceosome, and in the human 7SK gene, whose RNA product has been implicated in the regulation of the CDK9/cyclin T complex. They are also found in, for example, the H1 RNA gene, which encodes the RNA component of human RNase P, and the gene encoding the RNA component of human RNase MRP, as well as in genes encoding RNAs of unknown function.

The discovery of type-3 promoters came as a surprise because, unlike the then-characterized type 1 and 2 promoters, the type-3 core promoters turned out to be gene-external. They are located in the 5'-flanking region of the gene, and include a proximal sequence element (PSE), which also constitutes, on its own, the core of RNA polymerase II snRNA promoters, and a TATA box located at a fixed distance downstream of the PSE. Strikingly, in the vertebrate snRNA promoters, RNA polymerase specificity can be switched from RNA polymerase III to RNA polymerase II and vice versa by abrogation or generation of the TATA box. Upstream of the PSE is an element referred to as the distal sequence element (DSE), which activates transcription from the core promoter. Although the presence of a TATA box is the hallmark of type 3, gene-external promoters, it is also found in the 5'-flanking regions of some genes with gene-internal promoter elements.

As used herein, the term "internal leader promoter" includes certain Pol III type 3 promoters from yeast that drive the transcription of a primary transcript consisting of the leader sequence and the mature RNA. The internal leader promoter is subsequently cleaved posttranscriptionally from the primary transcript to yield the mature RNA product, Specific, non-limiting examples of internal leader promoters include the SNR52 promoter and the RPR1 promoter. SNR52 and RPR1 share a promoter organization that includes a leader sequence in which the A- and B-boxes are internal to the primary transcript, but are external to the mature RNA product. As shown herein, internal leader promoters can be exploited to express E. coli tRNAs in yeast.

Reporter: An agent that can be used to identify and/or select target components of a system of interest. For example, a reporter can include a protein, for instance, an enzyme, that confers antibiotic resistance or sensitivity (for instance, 3-lactamase, chloramphenicol acetyltransferase (CAT), and the like), a fluorescent screening marker (for instance, green fluorescent protein (GFP), YFP, EGFP, RFP, etc.), a luminescent marker (for instance, a firefly luciferase protein), an affinity based screening marker, or positive or negative selectable marker genes such as lacZ, 3-gal/lacZ (13-galactosidase), ADH (alcohol dehydrogenase), his3, ura3, leu2, lys2, or the like.

A reporter gene is a nucleic acid sequence that encodes a product (for instance firefly luciferase, CAT, and O-galactosidase), whose presence can be assayed. A reporter gene can be operably linked to a regulatory control sequence and introduced into cells. If the regulatory control sequence is transcriptionally active in a particular cell type, the reporter gene product normally will be expressed in such cells and its activity can be measured using techniques known in the art. The activity of a reporter gene product can be used, for example, to assess the transcriptional activity of an operably linked regulatory control sequence.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences. Methods for aligning sequences for comparison are described in detail below, in section IV J of the Detailed Description.

Selector codon: Codons recognized by the O-tRNA in the translation process and not recognized by an endogenous tRNA. The O-tRNA anticodon loop recognizes the selector codon on the mRNA and incorporates its amino acid, for instance, an unnatural amino acid, at this site in the peptide. Selector codons can include, for instance, nonsense codons, such as stop codons, for instance, amber, ochre, and opal codons; missense or frameshift codons; four-base codons; rare codons; codons derived from natural or unnatural base pairs and/or the like.

Stem cell: A cell that has the ability to self replicate indefinitely and that, under the right conditions, or given the right signals, can differentiate into some or all of the different cell types that make up an organism. Stem cells have the potential to develop into mature, differentiated cells, such as heart cells, skin cells, or nerve cells.

The fertilized egg is because it has the potential to generate all the cells and tissues that make up an embryo and that support its development in utero. Adult mammals include more than 200 kinds of cells, for instance, neurons, myocytes, epithelial cells, erythrocytes, monocytes, lymphocytes, osteocytes, and chondrocytes. Other cells that are essential for embryonic development but are not incorporated into the body of the embryo include the extraembryonic tissues, placenta, and umbilical cord. All of these cells are generated from a single fertilized egg.

Pluripotent cells can give rise to cells derived from all three embryonic germ layers—mesoderm, endoderm, and ectoderm. Thus, pluripotent cells have the potential to give rise to any type of cell.

Unipotent stem cells are capable of differentiating along only one lineage.

Embryonic stem cells are pluripotent cells derived from the blastocyst.

Adult stem cells are undifferentiated cells found in a differentiated tissue that can replicate and become specialized to yield all of the specialized cell types of the tissue from which it originated. Adult stem cells are capable of self-renewal for the lifetime of the organism. Sources of adult stem cells have been found in the bone marrow, blood stream, cornea, retina, dental pulp, liver, skin, gastrointestinal tract, and pancreas.

Suppressor tRNA: A suppressor tRNA is a tRNA that alters the reading of a messenger RNA (mRNA) in a given translation system, for instance, by providing a mechanism for incorporating an amino acid into a peptide chain in response to a selector codon. For example, a suppressor tRNA can read through, for instance, a stop codon (for instance, an amber, ocher or opal codon), a four-base codon, a missense codon, a frameshift codon, or a rare codon. Stop codons include, for example, the ochre codon (UAA), amber codon (UAG), and opal codon (UGA).

Transduction: The process by which genetic material, for instance, DNA or other nucleic acid molecule, is inserted into a cell. Common transduction techniques include the use of viral vectors (including bacteriophages), electroporation, and chemical reagents that increase cell permeability. Transfection and transformation are other terms for transduction, although these sometimes imply expression of the genetic material as well.

Transfer RNA (tRNA): A small RNA chain (generally 73-93 nucleotides) that transfers a specific amino acid to a growing peptide chain at the ribosomal site of protein synthesis during translation. It has a 3' terminal site for amino acid attachment. This covalent linkage is catalyzed by an aminoacyl tRNA synthetase. It also contains a three-base region called the anticodon that can base-pair to the corresponding three base codon region on mRNA. Each type of tRNA molecule can be attached to only one type of amino acid, but because the genetic code contains multiple codons that specify the same amino acid, tRNA molecules bearing different anticodons can also carry the same amino acid.

Transfer RNA has a primary structure, a secondary structure (usually visualized as the cloverleaf structure), and a tertiary structure (an L-shaped three-dimensional structure that allows the tRNA to fit into the P and A sites of the ribosome). The acceptor stem is a 7-bp stem made by the base pairing of the 5'-terminal nucleotide with the 3'-terminal nucleotide (which contains the CCA 3'-terminal group used to attach the amino acid). The acceptor stem can contain non-Watson-Crick base pairs. The CCA tail is a CCA sequence at the 3' end of the tRNA molecule that is used for the recognition of tRNA by enzymes involved in translation. In prokaryotes, the CCA sequence is transcribed, whereas in eukaryotes, the CCA sequence is added during processing and therefore does not appear in the tRNA gene.

An anticodon is a unit made up of three nucleotides that correspond to the three bases of the mRNA codon. Each tRNA contains a specific anticodon triplet sequence that can base-pair to one or more codons for an amino acid. For example, one codon for lysine is AAA; the anticodon of a lysine tRNA might be UUU. Some anticodons can pair with more than one codon due to a phenomenon known as wobble base pairing. Frequently, the first nucleotide of the anticodon is one of two not found on mRNA: inosine and pseudouridine, which can hydrogen bond to more than one base in the corresponding codon position. In the genetic code, it is common for a single amino acid to occupy all four third-position possibilities; for example, the amino acid glycine is coded for by the codon sequences GGU, GGC, GGA, and GGG. To provide a one-to-one correspondence between tRNA molecules and codons that specify amino acids, 61 tRNA molecules would be required per cell. However, many cells contain fewer than 61 types of tRNAs because the wobble base is capable of binding to several, though not necessarily all, of the codons that specify a particular amino acid.

Aminoacylation is the process of adding an aminoacyl group to a compound. It produces tRNA molecules with their CCA 3' ends covalently linked to an amino acid. Each tRNA is aminoacylated (or charged) with a specific amino acid by an aminoacyl tRNA synthetase. There is normally a single aminoacyl tRNA synthetase for each amino acid, despite the fact that there can be more than one tRNA, and more than one anticodon, for an amino acid. Recognition of the appropriate tRNA by the synthetases is not mediated solely by the anticodon, and the acceptor stem often plays a prominent role.

Unnatural amino acid (UAA): Any amino acid, modified amino acid, and/or amino acid analogue, that is not one of the 20 common naturally occurring amino acids or seleno cysteine or pyrrolysine. Unnatural amino acids are described at greater length in section IV F of the Detailed Description below.

Vector: A nucleic acid molecule capable of transporting a non-vector nucleic acid sequence which has been introduced into the vector. One type of vector is a "plasmid," which refers to a circular double-stranded DNA into which non-plasmid DNA segments can be ligated. Other vectors include cosmids, bacterial artificial chromosomes (BAC) and yeast artificial chromosomes (YAC). Another type of vector is a viral vector, wherein additional DNA segments can be ligated into all or part of the viral genome. Certain vectors are capable of autonomous replication in a host cell into which they are introduced (for example, vectors having a bacterial origin of replication replicate in bacteria hosts). Other vectors can be integrated into the genome of a host cell upon introduction into the host cell and are replicated along with the host genome. Some vectors contain expression control sequences (such as promoters) and are capable of directing the transcription of an expressible nucleic acid sequence that has been introduced into the vector. Such vectors are referred to as "expression vectors." A vector can also include one or more selectable marker genes and/or genetic elements known in the art.

Yeast: A eukaryotic microorganism classified in the Kingdom Fungi, with about 1,500 species described. Most reproduce asexually by budding, although a few reproduce by binary fission. Yeasts generally are unicellular, although some species may become multicellular through the formation of a string of connected budding cells known as pseudohyphae, or false hyphae. Exemplary yeasts that can be used in the disclosed methods and kits include but are not limited to *Saccharomyces cerevisiae, Candida albicans, Schizosaccharomyces pombe*, and *Saccharomycetales*.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8).

The singular terms "a," "an," and "the" include plural referents unless context clearly indicates otherwise. "Comprising" means "including." "Comprising A or B" means "including A," "including B" or "including A and B." It is further to be understood that all base sizes or amino acid sizes, and all molecular weight or molecular mass values, given for nucleic acids or peptides are approximate, and are provided for description.

Suitable methods and materials for the practice or testing of the disclosure are described below. However, the provided materials, methods, and examples are illustrative only and are not intended to be limiting. Accordingly, except as otherwise noted, the methods and techniques of the present disclosure can be performed according to methods and materials similar or equivalent to those described and/or according to conventional methods well known in the art and as described in various general and more specific references that are cited and discussed throughout the present specification (see, for instance, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999).

IV. Expression of Unnatural Amino Acids in Eukaryotic Cells

A. Overview

Described herein is a general strategy for efficient expression of prokaryotic tRNA, regardless of the internal promoter elements, in eukaryotic cells by using a pol III promoter. Exemplary pol III promoters include those that are not transcribed, but have a defined starting transcription site for direct RNA transcription, and those that are transcribed together with the tRNA, and are then cleaved post-transcriptionally to yield the tRNA.

For example, a pol III promoter can be operably linked to a prokaryotic tRNA, and the resulting construct introduced into a eukaryotic cell, thereby permitting expression of the prokaryotic tRNA in the cell. Most pol III promoters do not require downstream transcriptional elements, and have a well-defined transcription initiation site for generating the correct 5' end of tRNA. For example, the H1 promoter can drive the expression of different tRNAs (for instance, EctRNA$_{CUA}^{tyr}$ and EctRNA$_{CUA}^{leu}$) in various cell types (e.g., HeLa, HEK293, mouse and rat primary neurons) for the incorporation of diverse natural or unnatural amino acids. Other members of the type-3 class of pol III promoters, such as the promoter for U6 snRNA, 7SK, and MRP/7-2, also work in a similar manner.

In another example, an internal leader promoter can be operably linked to a prokaryotic tRNA, and the resulting construct introduced into a eukaryotic cell, thereby permitting expression of the prokaryotic tRNA in the cell. Internal leader promoters are transcribed together with the tRNA, and are then cleaved post-transcriptionally to yield the tRNA. For instance internal leader promoters such as the SNR52 promoter and the RPR1 promoter can drive the efficient expression of different tRNAs (for instance, EctRNA$_{CUA}^{tyr}$ and EctRNA$_{CUA}^{leu}$) in yeast cells for the incorporation of diverse natural or unnatural amino acids.

Co-expression a tRNA and a prokaryotic aminoacyl-tRNA synthetase in the same eukaryotic cell can be used to drive the incorporation of unnatural amino acids (UAAs) in proteins in the cell. For instance, the eukaryotic cell can genetically encode an UAA when: (1) the prokaryotic tRNA/aminoacyl-tRNA synthetase pair is specific for the UAA, (2) the prokaryotic tRNA decodes a blank codon unused by a common amino acid (such as stop codons or extended codons), (3) the prokaryotic tRNA/synthetase pair works with the protein biosynthesis machinery of the host cell, and (4) there is little or no crosstalk between the prokaryotic tRNA/synthetase and endogenous tRNA/synthetase pairs (i.e., the tRNA/synthetase pair is orthogonal).

To evolve a synthetase specific for a desired UAA, mutant synthetase libraries containing more than $10^9$ members previously were made and selected in *E. coli*, and later in yeast. Due to the low transfection efficiency, it is impractical to generate such huge libraries in mammalian cells and neurons. However, as described herein, synthetases evolved in yeast can be successfully transferred for use in mammalian cells and in neurons. This transfer strategy facilitates the incorporation of diverse UAAs tailored for mammalian and neuronal studies. Using these strategies, it is now possible, for the first time, to genetically encode UAAs in different eukaryotic cells, for example, mammalian cells and primary neurons. Furthermore, the method offers a dramatic improvement in the efficiency of UAA expression in yeast, for example in yeast substantially Nonsense-Mediated mRNA Decay—(NMD)-deficient.

The NMD pathway is a cellular mechanism of mRNA surveillance used by the cell to detect nonsense mutations and prevent the expression of truncated or erroneous proteins. Disruption of this pathway results in a higher efficiency of incorporation of UAAs in cells such as yeast cells and mammalian cells. The NMD pathway mediates the rapid degradation of mRNAs that contain premature stop codons in yeast, whereas no such pathway exists in *E. coli*. When stop codons are used to encode UAAs, in some examples, NMD results in a shorter lifetime for the target mRNA, and thus a lower protein yield in yeast. An NMD-deficient yeast strain is used in some embodiments to overcome this problem, and to enable high-yield production of UAAs in yeast.

This strategy also can be used effectively in mammalian cells. In mammalian cells, the efficacy of disrupting the NMD pathway depends on the presence of exon-intron junctions in the DNA sequence. Thus, if there are introns in the gene of interest, disrupting the NMD pathway increases the efficiency of UAA incorporation.

Although the methods described below demonstrate increased UAA incorporation efficiency when used with orthogonal tRNA/synthetase pairs and a pol III promoter, the efficiency of any strategy for the incorporation of UAAs (for instance, using a 5' flanking sequence methodology) is improved by de-activation of the NMD pathway, as described herein Genetically encoding UAAs removes restrictions imposed by in vitro semisynthetic and biosynthetic unnatural-amino-acid incorporation methods on protein type, size, quantity and location (Muir (2003) *Annu. Rev. Biochem.* 72, 249-289; Cornish et al., (1995) *Angewandte Chemie-International Edition in English* 34, 621-633). The compatibility of this method with living systems is valuable for proteins whose function requires native complex cellular environments such as integral membrane proteins and proteins involved in signaling. Genetic stability and inheritance are well-suited for researching long-term biological processes such as developmental and evolutionary studies.

In addition, this technology does not require special expertise, and is easily transferable to the scientific community in the form of plasmid DNA or stable cell lines. Thus, unnatural amino acids can be designed and encoded to probe and control proteins and protein-related biological processes. For instance, fluorescent unnatural amino acids can be used to sense local environmental changes and serve as reporters for enzyme activity, membrane potential or neurotransmitter release; unnatural amino acids bearing photocrosslinking agents can be applied to identify protein-protein and protein-nucleic acid interactions in cells; and photocaged and photoisomerizable amino acids can be designed to switch on and off signal initiation and transduction noninvasivelyo. Many of these unnatural amino acids previously have been encoded in *E. coli* and in yeast, albeit with low efficiency (Wang et al., (2006)*Annu. Rev. Biophys. Biomol. Struct.* 35, 225-249). The compositions and methods described herein enable the genetic encoding of such novel amino acids in mammalian cells and neurons, thus making possible more precise molecular studies of cell biology and neurobiology. Furthermore, improvements in the efficiency of unnatural amino acid expression in yeast enable large-scale preparation of modified polypeptides.

B. Orthogonal tRNA/Aminoacyl-tRNA Synthetase Pairs

An understanding of the novel compositions and methods disclosed herein is facilitated by an understanding of the activities associated with orthogonal tRNA and orthogonal aminoacyl-tRNA synthetase pairs. Discussions of orthogonal tRNA and aminoacyl-tRNA synthetase technologies can be found, for example, in International Publications WO 2002/085923, WO 2002/086075, WO 204/09459, WO 2005/019415, WO 2005/007870 and WO 2005/007624. See also, Wang & Schultz (2005) *Angewandte Chemie mt.* Ed., 44(1): 34-66, the content of which is incorporated by reference in its entirety.

In order to add additional reactive unnatural amino acids to the genetic code, orthogonal pairs including an aminoacyl-tRNA synthetase and a suitable tRNA are needed that can function efficiently in the host translational machinery, but that are "orthogonal" to the translation system at issue, meaning that it functions independently of the synthetases and tRNAs endogenous to the translation system. In particular examples, characteristics of the orthologous pair include tRNAs that decode or recognize only a specific codon, for instance, a selector codon, that is not decoded by any endogenous tRNA, and aminoacyl-tRNA synthetases that preferentially aminoacylate (or "charge") its cognate tRNA with only one specific unnatural amino acid. The O-tRNA also typically is not aminoacylated by endogenous synthetases. For example, in a eukaryotic cell, an orthogonal pair will, in certain examples, include an aminoacyl-tRNA synthetase that does not cross-react with endogenous tRNA, and an orthogonal tRNA that is not aminoacylated by endogenous synthetases. In some embodiments, the exogenous tRNA and aminoacyl-tRNA synthetase are prokaryotic. When expressed in a eukaryotic cell, the exogenous aminoacyl-tRNA synthetase aminoacylates the exogenous suppressor tRNA with its respective UAA and not with any of the common twenty amino acids.

The ability to express UAAs in eukaryotic cells and incorporate an UAA into a protein expressed in a eukaryotic cell can facilitate the study of proteins, as well as enable the engineering of proteins with novel properties. For example, expression of proteins containing one or more UAAs can facilitate the study of proteins by specific labeling, alter catalytic function of enzymes, improve biological activity or reduce cross-reactivity to a substrate, crosslink a protein with other proteins, small molecules or biomolecules, reduce or eliminate protein degradation, improve half-life of proteins in vivo (for instance, by pegylation or other modifications of introduced reactive sites), etc.

In general, when an orthogonal pair recognizes a selector codon and loads an amino acid in response to the selector codon, the orthogonal pair is said to "suppress" the selector codon. That is, a selector codon that is not recognized by the translation system's (for instance, the eukaryotic cell's) endogenous machinery is not ordinarily translated, which can result in blocking production of a peptide that would otherwise be translated from the nucleic acid. An O-tRNA of the disclosure recognizes a selector codon and includes at least about, for instance, a 45%, a 50%, a 60%, a 75%, a 80%, or a 90% or more suppression efficiency in the presence of a cognate synthetase in response to a selector codon as compared to the suppression efficiency of an O-tRNA comprising or encoded by a nucleic acid molecule sequence, for instance as set forth in the sequence listing as SEQ ID NOs 33 and 34.

The O—RS aminoacylates the O-tRNA with an UAA of interest, and the cell uses the O-tRNA/O—RS pair to incorporate the UAA into a growing peptide chain, for instance, via a nucleic acid molecule that includes a nucleic acid molecule that encodes a peptide of interest, where the nucleic acid molecule includes a selector codon that is recognized by the O-tRNA. In certain embodiments, the cell can include an additional O-tRNA/O—RS pair, where the additional O-tRNA is loaded by the additional O—RS with a different UAA. For example, one of the O-tRNAs can recognize a four-base codon and the other can recognize a stop codon. Alternately, multiple different stop codons or multiple different four base codons can specifically recognize different selector codons. In one embodiment, the suppression efficiency of the O—RS and the O-tRNA together is at least 5-fold, 10-fold, 15-fold, 20-fold, or 25-fold (or more) greater than the suppression efficiency of the O-tRNA lacking the O—RS.

Suppression efficiency can be determined by any of a number of assays known in the art, for example, a β-galactosidase reporter assay. A cognate synthetase can also be introduced (either as a peptide or a nucleic acid molecule that encodes the cognate synthetase when expressed). The cells are grown in media to a desired density, and β-galactosidase assays are performed. Percent suppression can be calculated as the percentage of activity for a sample relative to a suitable control, for instance, the value observed from the derivatized lacZ construct, where the construct has a corresponding sense codon at desired position rather than a selector codon.

The O-tRNA and/or the O—RS can be naturally occurring or can be derived by mutation of a naturally occurring prokaryotic tRNA and/or RS, for instance, by generating libraries of tRNAs and/or libraries of RSs, from any of a variety of organisms and/or by using any of a variety of available mutation methods. For example, one method for producing an orthogonal tRNA/aminoacyl-tRNA synthetase pair involves importing a heterologous (to the host cell) tRNA/synthetase pair from a source other than the host cell, or multiple sources, into the host cell. The properties of the heterologous synthetase candidate include that it does not charge any host cell tRNA, and the properties of the heterologous tRNA candidate include that it is not aminoacylated by any host cell synthetase. In addition, the heterologous tRNA is orthogonal to all host cell synthetases. A second strategy for generating an orthogonal pair involves generating mutant libraries from which to screen and/or select an O-tRNA or O—RS. These strategies also can be combined.

A number of orthogonal tRNA/aminoacyl-tRNA synthetase pairs have been identified, including but not limited to the tyrosyl tRNA/TyrRS derived from *E. coli*, the leucyl tRNA/TyrRS derived from *E. coli*, the glutaminyl tRNA/GlnRS derived from *E. coli* (Kohrer et al., (2004) *Nucleic Acids Res.* 32(21):6200-11), the tryptophanyl tRNA/TrpRS derived from *B. subtilis* (Zhang et al., (2004)*Proc Natl Acad Sci USA.* 101(24):8882-7), the *M. jannaschii* tyrosyl tRNA/TyrRS for use in *E. coli*, and the *E. coli* tyrosyl tRNA/TyrRS for use in yeast.

C. Source and Host Cells

The orthogonal translational components (O-tRNA and O—RS) of the disclosure can be derived from any organism (or a combination of organisms) for use in a host translation system from any other species, with the caveat that the O-tRNA/O—RS components and the host system work in an orthogonal manner. It is not a requirement that the O-tRNA and the O—RS from an orthogonal pair be derived from the same organism. In some embodiments, the orthogonal components are derived from Archaea genes (for instance, archaebacteria) for use in a eukaryotic host system.

For example, the orthogonal O-tRNA and the orthogonal O—RS can be derived from an *Archae* organism, such as *Methanococcus jannaschii, Methanobacterium thermoautotrophicum, Halobacteriurn* such as *Haloferax volcanii* and *Halobacterium* species NRC-i, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a *eubacterium*, such as *Escherichia coli, Thermus thermophilus, Bacillus stearotherinphilus*, or the like. The individual components of an O-tRNA/O—RS pair can be derived from the same organism or different organisms.

The eukaryotic host cell can be from any eukaryotic species, for example, animals (for instance, mammals, insects, reptiles, birds, etc.), plants (for instance, monocots, dicots, algae, etc.), fungi, yeasts, flagellates, microsporidia, and protists, etc. In certain embodiments, the eukaryotic host cell is a mammalian cell, for example a human, cat, dog, mouse, rat, sheep, cow, or horse cell. In certain embodiments, the host cell is a neuron. In other embodiments, the host cell is a stem cell. In a particular embodiment, the host cell is a yeast cell, for instance an *S. cerevisiae, S. pombe, C. albicans*, or *Saccharomycetale* cell. In some examples, the cell is a eukaryotic cell that is substantially Nonsense-Mediated mRNA Decay—(NMD)-deficient, such as a yeast or mammalian cell that is NMD-deficient.

As described at greater length below in Example 6, the NMD pathway is an evolutionarily conserved mRNA surveillance pathway that recognizes and eliminates aberrant mRNAs harboring premature termination codons, thereby preventing the accumulation of nonfunctional or potentially deleterious truncated proteins in the cells. In addition to mRNAs with premature termination codons, NMD degrades a variety of naturally occurring transcripts to suppress genomic noise. One step in NMD is the translation-dependent recognition of transcripts with aberrant termination events and then targeting those mRNAs for destruction.

As is well known in the art, the three Upf proteins, Upf 1, Upf2 and Upf3, constitute the core NMD machinery as they are conserved and required for NMD in *Saccharomyces cerevisiae, Drosophila melanogaster*, and in mammalian cells. Upf1 appears to recognize aberrant translation termination events and, then in a subsequent step, interacts with Upf2 and Upf3 to trigger degradation of mRNA. Specific, non-limiting examples of Upf1 sequences include GenBank Accession Nos: AAF48115 (*D. melanogaster*), EAW84742 (human), AAH52149 (mouse), and CAA91194 (*S. pombe*). Specific, non-limiting examples of Upf2 sequences include GenBank Accession Nos: AAF46314 (*D. melanogaster*), AAG60689 (human), CAM23670 (mouse), and CAB11644 (*S. pombe*). Specific, non-limiting examples of Upf3 sequences include GenBank Accession Nos: AAM68275 (*D. melanogaster*), AAG60690 (human), AAI19036 (mouse), and CAA97074 (*S. cerevisiae*).

In yeast, a lack of mRNA stability of the target gene can interfere with the efficiency of UAA incorporation. The NMD pathway mediates the rapid degradation of mRNAs that contain premature stop codons in yeast, whereas no such pathway exists in *E. coli*. When stop codons are used to encode UAAs, in some examples, NMD results in a shorter lifetime for the target mRNA, and thus a lower protein yield in yeast. Thus, an NMD-deficient yeast strain is used in some embodiments to overcome this problem, and to enable high-yield production of UAAs in yeast.

This strategy also can be used effectively in mammalian cells. In mammalian cells, the efficacy of disrupting the NMD pathway depends on the presence of exon-intron junctions in the DNA sequence. Thus, if there are introns in the gene of interest, disrupting the NMD pathway increases the efficiency of UAA incorporation.

Complete NMD deficiency in the cell is not required, and in some examples is avoided (for example if complete NMD deficiency is toxic to the cell). For example, partial NMD deficiency can be sufficient to achieve the desired result, such as enhancing prokaryotic tRNA expression in a eukaryotic cell, enhancing the efficiency of incorporation of a UAA a eukaryotic cell, or both.

Methods of decreasing expression or activity of a gene in a eukaryotic cell are well known in the molecular biology arts. In addition, such methods are enabled by the public availability of genes in the NMD-pathway (for example on GenBank or EMBL). In addition, such methods are enabled by the public availability of genes in the NMD-pathway (for example on GenBank or EMBL).

For example, NMD-deficient cells (such as yeast or mammalian cells) and be engineered to lack the UPF1 gene, which in some examples is essential for the function of the NMD pathway. Other methods for deactivating the NMD pathway include the complete knock out, partial deletion, partial mutation, or silencing (e.g., through RNA interference) of any genes involved in the NMD pathway, such as upf1, upf2, upf3, hrp1, nmd2, etc., and using small molecules to inhibit the function of proteins involved in the NMD pathway, such as the function of Upf1p, Upf2p, Upf3p, Hrp1p, Nmd2p, etc. Methods of reducing the expression of a protein using molecular biological techniques are conventional, and are well known in the art.

Some embodiments include cell lines that are substantially NMD-deficient, such as NMD-deficient mammalian cell lines and NMD-deficient yeast cell lines. A labeled UAA, such as a fluorescent UAA, can be incorporated in the NMD-deficient strain, and the intensity of the label can be used as a measure of UAA incorporation efficiency.

D. Promoters

A promoter is a region of DNA that generally is located upstream (towards the 5' region of a gene) and is needed for transcription. Promoters permit the proper activation or repression of the gene which they control. A promoter contains specific sequences that are recognized by transcription factors. These factors bind to the promoter DNA sequences and result in the recruitment of RNA polymerase, the enzyme that synthesizes the RNA from the coding region of the gene. Promoters useful in carrying out the methods described herein include RNA polymerase III (also called pol III) promoters, which transcribe DNA to synthesize ribosomal 5S rRNA, tRNA, and other small RNAs, generally structural or catalytic RNAs that are, generally, shorter than 400 base pairs. Pol III is unusual in that it requires no control sequences upstream of the gene. Instead it normally relies on internal control sequences.

The classification of pol III genes by their promoter structure has been covered in several reviews (see, for example, Geiduschek & Tocchini-Valentini (1988) *Annu. Rev. Biochem.* 57, 873-914). Most genes transcribed by pol III fall into one of three well defined groups, depending on the location or type of cis-acting elements which constitute their promoters. Type-1 genes include 5s RNA genes whose promoters are distinguished by three intragenic sequence elements; a 5' A block, an intermediate element and a 3° C. block. These elements span a region of approximately 50 bp beginning at about position +45. Type-2 genes are identified by well conserved A and B block elements. The A block is invariantly intragenic and, in contrast to 5s genes, is positioned closer to the transcription start site (usually at about 10-20 bp). Type-3 genes are characterized by promoter sequences that reside upstream of the coding sequence. The prototypes of this group include metazoan U6 small-nuclear RNA genes and the human 7SK gene. The promoters of these genes contain a TATA sequence near position −30 that determines the polymerase specificity of the transcription unit, and a proximal sequence element at around position −60. Together, these two elements constitute a basal promoter which is subject to activation by a variety of factors that bind to distal sequence elements.

A dichotomy exists concerning the transcription of genes identified initially as belonging to the type-3 class in metazoans and these same genes in yeast. Instead of the upstream control regions that are the hallmark of the type-3 class, the homologs of type-3 genes in yeast rely on A-block and B-block promoter elements typical of type-2 transcription units. The first reported example was the U6 gene from *Saccharomyces cerevisiae*, which contains a B-block element positioned 120-bp downstream of the coding sequence, beyond the site of transcription termination. Fission yeast also are likely to use A-block and B-block elements to direct U6 gene transcription.

Another example of a gene whose mode of transcription differs depending on the organism from which it is derived is the gene encoding the RNA component of RNase P. The human gene for this RNA, designated H1, contains multiple cis-acting elements upstream of the start site and does not require internal sequences for transcription in vitro. By this criterion, the H1 RNA gene is a typical type-3 gene. However, the homologous gene from *S. cerevisiae* (RPR1) relies on A-block and B-block elements positioned upstream of the mature RNase P RNA sequence to direct transcription.

In some embodiments described herein, the promoter is a type-3 pol III H1 promoter. The H1 promoter can drive the expression of different tRNAs in various cell types (for instance, HeLa, HEK293, mammalian primary neurons) for the incorporation of diverse natural or UAAs. Other members of the type-3 class of pol III promoter are also useful in the practice of the disclosed methods, and include, for instance, the promoters for U6 snRNA, 7SK, and MRP/7-2, as well as internal leader promoters.

Certain yeast pol III type 3 promoters are transcribed together with the tRNA, and are then cleaved post-transcriptionally to yield the tRNA. Such promoters, for instance, the SNR52 promoter and the RPR1 promoter, can be used for efficient incorporation of UAAs in yeast cells. Internal leader promoters such as SNR52 and RPR1 share a promoter organization that includes a leader sequence in which the A- and B-boxes are internal to the primary transcript, but are external to the mature RNA product.

E. Selector Codons

Selector codons of the disclosure expand the genetic codon framework of protein biosynthetic machinery. Exemplary selector codons include a unique three base codon, a nonsense codon, such as a stop codon, for instance, an ochre codon (UAA), an amber codon (UAG), or an opal codon (UGA), a missense or frameshift codon, an unnatural codon, a four-base codon, a rare codon, or the like. A number of selector codons can be introduced into a desired gene, and by using different selector codons, multiple orthogonal tRNA/synthetase pairs can be used that allow the simultaneous site-specific incorporation of multiple UAAs.

In one embodiment, the methods include the use of a selector codon that is a stop codon for the incorporation of a UAA in vivo in a cell. For example, an O-tRNA is produced that recognizes the stop codon and is aminoacylated by an O—RS with a UAA. This O-tRNA is not recognized by the naturally occurring host's aminoacyl-tRNA synthetases. When the O—RS, O-tRNA and the nucleic acid molecule that encodes a peptide of interest are combined, for instance, in vivo, the UAA is incorporated in response to the stop codon to give a peptide containing the UAA at the specified position. In one embodiment, the stop codon used as a selector codon is an amber codon, UAG, and/or an opal codon, UGA.

F. Unnatural Amino Acids (UAAs)

As used herein, an unnatural amino acid (UAA) refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I: $H_2NCH(R)COOH$.

A UAA typically is any structure having Formula I wherein the R group is any substituent other than one used in the twenty natural amino acids. See for instance, Biochemistry by L. Stryer, 31 (1 ed. 1988), Freeman and Company, New York, for structures of the twenty natural amino acids. UAAs also can be naturally occurring compounds other than the twenty alpha-amino acids above.

Specific, non-limiting examples of UAAs include p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenylalanine. Both the L and D-enantiomers of these UAAs are included in the disclosure. Many additional UAAs and suitable orthogonal pairs are known. For example, see Wang & Schultz (2005) Angewandte Cheinie mt. Ed., 44(1): 34-66, the content of which is incorporated by reference in its entirety.

In some UAAs, R in Formula I optionally includes an alkyl-, aryl-, acyl-, hydrazine, cyano-, halo-, hydrazide, alkenyl, ether, borate, boronate, phospho, phosphono, phosphine, enone, imine, ester, hydroxylamine, or amine group or the like, or any combination thereof. Other UAAs of interest include, but are not limited to, amino acids comprising a crosslinking amino acid, photoactivatable crosslinking amino acids, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, photoaffinity labeled amino acids, biotin or biotin-analogue containing amino acids, polymer-containing amino acids, cytotoxic molecule-containing amino acids, saccharide-containing amino acids, heavy metal-binding element-containing amino acids, amino acids containing a heavy atom, amino acids containing a redox group, amino acids containing an infrared probe, amino acids containing an azide group, amino acids containing an alkyne group, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (for instance, polyethers or long chain hydrocarbons, for instance, greater than about 5, greater than about 10 carbons, etc.), carbon-linked sugar-containing amino acids, amino thioacid containing amino acids, and amino acids containing one or more toxic moieties.

In addition to UAAs that contain novel side chains, UAAs also can optionally include modified backbone structures, for instance, as illustrated by the structures of Formulas II and III:

    II

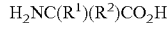    III wherein Z typically includes OH, NH$_2$, SH, NH—R$^2$, or S—R$^2$; X and Y, which can be the same or different, typically include S or O, and R$^1$ and R$^2$, which are optionally the same or different, are typically selected from the same list of constituents for the R group described above for the UAAs having Formula I as well as hydrogen. For example, unnatural amino acids optionally include substitutions in the amino or carboxyl group as illustrated by Formulas II and III. UAAs of this type include, but are not limited to, α-hydroxy acids, α-thioacids α-aminothiocarboxylates, for instance, with side chains corresponding to the common twenty natural amino acids or unnatural side chains. In addition, substitutions at the α-carbon optionally include L, D, or α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, 3 and γ amino acids such as substituted β-alanine and γ-amino butyric acid. In some embodiments, the UAAs are used in the L-configuration. However, the disclosure is not limited to the use of L-configuration UAAs, and D-enantiomers of these UAAs also can be used.

Tyrosine analogs include para-substituted tyrosines, ortho-substituted tyrosines, and meta substituted tyrosines, wherein the substituted tyrosine includes an alkynyl group, acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenylalanines, and meta-substituted phenylalanines, wherein the substituent includes an alkynyl group, a hydroxy group, a methoxy group, a methyl group, an allyl group, an aldehyde, a nitro, a thiol group, or keto group, or the like. Specific examples of UAAs include, but are not limited to, p-ethylthiocarbonyl-L-phenylalanine, p-(3-oxobutanoyl)-L-phenylalanine, 1,5-dansyl-alanine, 7-amino-coumarin amino acid, 7-hydroxy-coumarin amino acid, nitrobenzyl-serine, O-(2-nitrobenzyl)-L-tyrosine, p-carboxymethyl-L-phenylalanine, p-cyano-L-phenylalanine, m-cyano-L-phenylalanine, biphenylalanine, 3-amino-L-tyrosine, bipyridyl alanine, p-(2-amino-1-hydroxyethyl)-L-phenylalanine, p-isopropylthiocarbonyl-L-phenylalanine, 3-nitro-L-tyrosine and p-nitro-L-phenyl alanine. Also, a p-propargyloxyphenylalanine, a 3,4-dihydroxy-L-phenyalanine (DIHP), a 3,4,6-trihydroxy-L-phenylalanine, a 3,4,5-trihydroxy-L-phenylalanine, 4-nitro-phenylalanine, a p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a 3-nitro-tyrosine, a 3-thiol-tyrosine, a tn-O—acetyl-GlcNAc-serine, an L-Dopa, a fluorinated phenylalanine, an isopropyl-L-phenylalanine, a p-azido-L-phenyl alanine, a p-acyl-L-phenylalanifle, a p-benzoyl-L-phenylalanine, an L-phosphoserifle, a phosphonoserine, a phosphonotyrosine, a p-iodo-phenylalanine, a p-bromophenylalanine, a p-amino-L-phenylalanine, and an isopropyl-L-phenylalanine, and the like. See also, Published International Application WO 2004/094593.

G. Chemical Synthesis of Unnatural Amino Acids (UAAs)

Many of the UAAs provided above are commercially available, for instance, from Sigma (USA) or Aldrich (Milwaukee, Wis., USA). Those that are not commercially available are optionally synthesized as provided in various publications or using standard methods. For organic synthesis techniques, see, for instance, Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of UAAs include, for instance, WO 2002/085923 entitled "In vivo incorporation of Unnatural Amino Acids;" Matsoukas et al., (1995) *J. Med. Chem.*, 38, 4660-4669; King & Kidd (1949) *J. Chem. Soc.*, 3315-3319; Friedman & Chatterrji (1959) *J. Am. Chem. Soc.* 81, 3750-3752; Craig et al., (1988) *J. Org. Chem.* 53, 1167-1170; Azoulay et al., (1991) *Eur. J. Med. Chem.* 26, 201-5; Koskinen & Rapoport (1989) *J. Org. Chem.* 54, 1859-1866; Christie & Rapoport (1985) *J. Org. Chem.* 1989:1859-1866; Barton et al., (1987) *Tetrahedron Lett.* 43:4297-4308; and, Subasinghe et al., (1992) *J. Med. Chem.* 3 5:4602-7.

H. Cellular Uptake of Unnatural Amino Acids (UAAs)

UAA uptake by a cell can be considered when designing and selecting UAAs, for instance, for incorporation into a protein. For example, the high charge density of α-amino acids indicates that these compounds are unlikely to be cell permeable. Natural amino acids are taken up into the cell via a collection of protein-based transport systems often displaying varying degrees of amino acid specificity. A rapid screen can be done to identify which UAAs, if any, are taken up by cells. See, for instance, the toxicity assays in International Publication WO 2004/058946, entitled "PROTEIN ARRAYS," filed on Dec. 22, 2003; and Liu & Schultz (1999) *PNAS* 96:47 80-4785. Although uptake is easily analyzed with various assays, an alternative to designing UAAs that are amenable to cellular uptake pathways is to provide biosynthetic pathways to create amino acids in vivo.

I. Biosynthesis of Unnatural Amino Acids (UAAs)

Many biosynthetic pathways already exist in cells for the production of amino acids and other compounds. While a biosynthetic method for a particular UAA may not exist in nature, for instance, in a cell, such methods are contemplated. For example, biosynthetic pathways for UAAs can be optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923) relies on the addition of a combination of known enzymes from other organisms. The genes for these enzymes can be introduced into a cell by transforming the cell with a plasmid that includes the genes. The genes, when expressed in the cell, provide an enzymatic pathway to synthesize the desired compound. Artificially evolved enzymes are also optionally added into a cell in the same manner. In this manner, the cellular machinery and resources of a cell are manipulated to produce UAAs.

J. Nucleic Acid Sequences and Variants

As any molecular biology textbook teaches, a peptide of interest is encoded by its corresponding nucleic acid sequence (for instance, an mRNA or genomic DNA). Accordingly, nucleic acid sequences encoding O-tRNAs and O—RSs are contemplated herein, at least, to make and use the O-tRNAs and O—RS peptides of the disclosed compositions and methods.

In one example, in vitro nucleic acid amplification (such as polymerase chain reaction (PCR)) can be utilized as a method for producing nucleic acid sequences encoding O-tRNAs and O—RSs. PCR is a standard technique, which is described, for instance, in PCR Protocols: *A Guide to Methods and Applications* (Innis et al., San Diego, Calif.: Academic Press, 1990), or *PCR Protocols, Second Edition* (*Methods in Molecular Biology, Vol.* 22, ed. by Bartlett and Stirling, Humana Press, 2003).

A representative technique for producing a nucleic acid sequence encoding an O-tRNA or O—RS by PCR involves preparing a sample containing a target nucleic acid molecule that includes the O-tRNA or O—RS sequence. For example, DNA or RNA (such as mRNA or total RNA) can serve as a suitable target nucleic acid molecule for PCR reactions. Optionally, the target nucleic acid molecule can be extracted from cells by any one of a variety of methods well known to those of ordinary skill in the art (for instance, Sambrook et al., *Molecular Cloning: A Laboratory Manual*, Cold Spring Harbor Laboratory Press, New York, 1989; Ausubel et al., *Current Protocols in Molecular Biology*, Greene Publ. Assoc. and Wiley-Intersciences, 1992). O-tRNAs and O—RSs are expressed in a variety of cell types; for example, prokaryotic and eukaryotic cells. In examples where RNA is the initial target, the RNA is reverse transcribed (using one of a myriad of reverse transcriptases commonly known in the art) to produce a double-stranded template molecule for subsequent amplification. This particular method is known as reverse transcriptase (RT)-PCR. Representative methods and conditions for RT-PCR are described, for example, in Kawasaki et al. (In *PCR Protocols, A Guide to Methods and Applications*, Innis et al. (eds.), 21-27, Academic Press, Inc., San Diego, Calif., 1990).

The selection of amplification primers will be made according to the portion(s) of the target nucleic acid molecule that is to be amplified. In various embodiments, primers (typically, at least 10 consecutive nucleotides of an O-tRNA or O—RS nucleic acid sequence) can be chosen to amplify all or part of an O-tRNA or O—RS-encoding sequence. Variations in amplification conditions may be required to accommodate primers and amplicons of differing lengths and composition; such considerations are well known in the art and are discussed for instance in Innis et al. (*PCR Protocols, A Guide to Methods and Applications*, San Diego, Calif.: Academic Press, 1990). From a provided O-tRNA or O—RS nucleic acid sequence, one skilled in the art can easily design many different primers that can successfully amplify all or part of a O-tRNA or O—RS-encoding sequence.

As described herein, disclosed are nucleic acid sequences encoding O-tRNAs and O—RSs. (See, for instance, SEQ ID NOs: 33 and 34.) Though particular nucleic acid sequences are disclosed herein, one of skill in the art will appreciate that also provided are many related sequences with the functions described herein, for instance, nucleic acid molecules encoding conservative variants of an O-tRNA or an O—RS disclosed herein. One indication that two nucleic acid molecules are closely related (for instance, are variants of one another) is sequence identity, a measure of similarity between two nucleic acid sequences or between two amino acid sequences expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al., *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 50%, at least 60%, at least 70%, at least 80%, at least 85%, at least 90%, at least 95%, at least 98%, or at least 99% sequence identity to the sequence of interest, for example the O—RS of interest.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, at least 98%, or at least 99% sequence identity to the O-tRNA or O—RS of interest.

Another indication of sequence identity is hybridization. In certain embodiments, O-tRNA or O—RS nucleic acid variants hybridize to a disclosed (or otherwise known) O-tRNA or O—RS nucleic acid sequence, for example, under low stringency, high stringency, or very high stringency conditions. Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, although wash times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11.

The following are representative hybridization conditions and are not meant to be limiting.

| Very High Stringency (detects sequences that share at least 90% sequence identity) | |
|---|---|
| Hybridization: | 5× SSC at 65° C. for 16 hours |
| Wash twice: | 2× SSC at room temperature (RT) for 15 minutes each |
| Wash twice: | 0.5× SSC at 65° C. for 20 minutes each |
| | High Stringency |
| | (detects sequences that share at least 80% sequence identity) |
| Hybridization: | 5×-6× SSC at 65° C.-70° C. for 16-20 hours |
| Wash twice: | 2× SSC at RT for 5-20 minutes each |
| Wash twice: | 1× SSC at 55° C.-70° C. for 30 minutes each |
| | Low Stringency |
| | (detects sequences that share at least 50% sequence identity) |
| Hybridization: | 6× SSC at RT to 55° C. for 16-20 hours |
| Wash at least twice: | 2×-3× SSC at RT to 55° C. for 20-30 minutes each. |

One of ordinary skill in the art will appreciate that O-tRNA or O—RS nucleic acid sequence of various lengths are useful for a variety purposes, such as for use as that O-tRNA or O—RS probes and primers. In some embodiments, an oligonucleotide can include at least 15, at least 20, at least 23, at least 25, at least 30, at least 35, at least 40, at least 45, at least 50 or more consecutive nucleotides of an O-tRNA or O—RS nucleic acid sequence. In other examples, O-tRNA or O—RS oligonucleotides (such as those encoding O-tRNA or O—RS functional fragments) can be at least 100, at least 150, at least 200, at least 250 or at least 300 consecutive nucleic acids of an O-tRNA or O—RS nucleic acid sequence.

K. Peptides

This disclosure further provides compositions and methods involving O—RS peptides. In some embodiments, O—RS variants include the substitution of one or several amino acids for amino acids having similar biochemical properties (so-called conservative substitutions). Conservative amino acid substitutions are likely to have minimal impact on the activity of the resultant protein. Further information about conservative substitutions can be found, for instance, in Ben Bassat et al. (*J. Bacteriol.*, 169:751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. In some examples, O—RS variants can have no more than 3, 5, 10, 15, 20, 25, 30, 40, or 50 conservative amino acid changes. The following table shows exemplary conservative amino acid substitutions that can be made to an O—RS peptide:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

L. Vectors

Host cells (for instance, eukaryotic cells) are provided that are genetically engineered (for instance, transformed, transduced or transfected) with one or more nucleic acid molecules encoding a pol III promoter, O-tRNA, and/or an O—RS (for instance, an O—RS that is specific for a UAA), or constructs which include a nucleic acid molecule encoding an O-tRNA and/or an O—RS (for instance, a vector) which can be, for example, an expression vector. For example, the coding regions for the orthogonal tRNA, the orthogonal tRNA synthetase, and the protein to be derivatized are operably linked to gene expression control elements that are co-transduced into the desired host cell, for instance a prokaryotic pol III promoter such as a type-3 pol III promoter or an internal leaderpromoter.

Methods of expressing proteins in heterologous expression systems are well known in the art. Typically, a nucleic acid molecule encoding all or part of a protein of interest is obtained using methods such as those described herein. The protein-encoding nucleic acid sequence is cloned into an expression vector that is suitable for the particular host cell of interest using standard recombinant DNA procedures. Expression vectors include (among other elements) regulatory sequences (for instance, prokaryotic promoters, such as a pol III promoter or internal leader promoter) that can be operably linked to the desired protein-encoding nucleic acid molecule to cause the expression of such nucleic acid molecule in the host cell. Together, the regulatory sequences and the protein-encoding nucleic acid sequence are an "expression cassette." Expression vectors can also include an origin of replication, marker genes that provide phenotypic selection in transformed cells, one or more other promoters, and a polylinker region containing several restriction sites for insertion of heterologous nucleic acid sequences.

Expression vectors useful for expression of heterologous protein(s) (such as those that include a UAA) in a multitude of host cells are well known in the art, and some specific examples are provided herein. The host cell is transfected with (or infected with a virus containing) the expression vector using any method suitable for the particular host cell. Such transfection methods are also well known in the art and non-limiting exemplar methods are described herein. The transfected (also called, transformed) host cell is capable of expressing the protein encoded by the corresponding nucleic acid sequence in the expression cassette. Transient or stable transfection of the host cell with one or more expression vectors is contemplated by the present disclosure.

Many different types of cells can be used to express heterologous proteins, such as yeasts and vertebrate cells (such as mammalian cells), including (as appropriate) primary cells and immortal cell lines. Numerous representatives of each cell type are commonly used and are available from a wide variety of commercial sources, including, for example, ATCC, Pharmacia, and Invitrogen.

Various yeast strains and yeast-derived vectors are used commonly for the expression of heterologous proteins. For instance, *Pichia pastoris* expression systems, obtained from Invitrogen (Carlsbad, Calif.), can be used to express an O—RS peptide. Such systems include suitable *Pichia pastoris* strains, vectors, reagents, transformants, sequencing primers, and media. Available strains include KM71H (a prototrophic strain), SMD1168H (a prototrophic strain), and SMD1168 (a pep4 mutant strain) (Invitrogen).

*Schizosaccharomyces pombe* and *Saccharomyces cerevisiae* are other yeasts that are commonly used. The plasmid YRp7 (Stinchcomb et al., *Nature,* 282:39, 1979; Kingsman et al., *Gene,* 7:141, 1979; Tschemper et al., *Gene,* 10: 157, 1980) is commonly used as an expression vector in *Saccharomyces*. This plasmid contains the trp1 gene that provides a selection marker for a mutant strain of yeast lacking the ability to grow in tryptophan, such as strains ATCC No. 44,076 and PEP4-1 (Jones, *Genetics,* 85:12, 1977). The presence of the trp1 lesion as a characteristic of the yeast host cell genome then provides an effective environment for detecting transformation by growth in the absence of tryptophan.

Yeast host cells can be transformed using the polyethylene glycol method, as described by Hinnen (*Proc. Natl. Acad. Sci. USA,* 75:1929, 1978). Additional yeast transformation protocols are set forth in Gietz et al. (*Nucl. Acids Res.,* 20(17):1425, 1992) and Reeves et al. (*FEMS,* 99(2-3):193-197, 1992).

In the construction of suitable expression vectors, the termination sequences associated with these genes are also ligated into the expression vector 3' of the sequence desired to be expressed to provide polyadenylation of the mRNA and termination. Any plasmid vector containing a yeast-compatible promoter (such as a pol III promoter or an internal leader promoter) capable of efficiently transcribing a nucleic acid sequence encoding a prokaryotic tRNA, an origin of replication, and a termination sequence is suitable.

Mammalian host cells can also be used for heterologous expression of an O—RS peptide. Examples of suitable mammalian cell lines include, without limitation, monkey kidney CV1 line transformed by SV40 (COS-7, ATCC CRL 1651); human embryonic kidney line 293S (Graham et al., *J. Gen. Virol.,* 36:59, 1977); baby hamster kidney cells (BHK, ATCC CCL 10); Chinese hamster ovary cells (Urlab and Chasin, *Proc. Natl. Acad. Sci. USA,* 77:4216, 1980); mouse sertoli cells (TM4, Mather, *Biol. Reprod.,* 23:243, 1980); monkey kidney cells (CV1-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.,* 85:1, 1980); and TRI cells (Mather et al., *Annals N.Y. Acad. Sci.,* 383:44, 1982), and primary culture cells such as neurons, for instance hippocampal neurons, spinal neurons, cortical neurons, cerebellar neurons, motomeurons, sensory neurons, pyramidal neurons, and retinal neurons. Expression vectors for these cells ordinarily include (if necessary) DNA sequences for an origin of replication, a promoter capable of transcribing a nucleic acid sequence encoding a prokaryotic tRNA, wherein the promoter sequence usually is located 5' of the nucleic acid sequence to be expressed, a ribosome binding site, an RNA splice site, a polyadenylation site, and/or a transcription terminator site.

M. Kits

Kits are also a feature of this disclosure. For example, a kit for producing a protein that includes at least one UAA in a eukaryotic cell is provided, where the kit includes a plasmid that includes a nucleic acid molecule that encodes a pol III promoter and a nucleic acid molecule that encodes a prokaryotic tRNA. In one embodiment, the kit further includes a nucleic acid molecule that encodes an aminoacyl-tRNA synthetase, for example, an aminoacyl-tRNA synthetase specific for the UAA to be expressed in the eukaryotic cell. In some embodiments, the tRNA and the aminoacyl-tRNA synthetase form an orthogonal pair.

A kit can also include, in certain embodiments, eukaryotic cells (for example, but not limited to yeast or mammalian cell lines) with orthogonal tRNA and unnatural-amino-acid-specific synthetase genes integrated into the chromosome. In a specific example, the kit includes eukaryotic cells (for examples mammalian cells or yeast cells) with an inactivated NMD pathway. Kits such as these enable a user to transfect a gene of interest to make proteins containing UAAs. In some examples, the elements of a kit are provided in separate containers.

The following examples are provided to illustrate certain particular features and/or embodiments. These examples should not be construed to limit the disclosure to the particular features or embodiments described.

EXAMPLES

Example 1

Materials and Methods

This Example describes materials and methods that were used in performing Examples 2-4. Although particular methods are described, one of skill in the art will understand that other, similar methods also can be used.

Chemicals

OmeTyr and Bpa were purchased from Chem-Impex. DanAla was synthesized using a procedure previously described (see, for instance, Summerer et al. (2006) *Proc. Natl. Acad. Sci. U.S.A.* 103, 9785-9789). All other chemicals were purchased from Sigma-Aldrich.

Constructs

All constructs were assembled by standard cloning methods and confirmed by DNA sequencing. Plasmid pCLHF is a derivative of pCLNCX (Imgenex), and contains the hygromycin resistance gene instead of the neomycin resistance gene. The amber stop codon TAG was introduced into the enhanced GFP (EGFP) gene at position 182 through site-directed mutagenesis. The woodchuck hepatitis virus post-transcriptional regulatory element (WPRE; Zufferey et al., (1999) *J. Virol.* 73, 2886-2892) was added to the 3' end of the GFP-TAG mutant gene. The GFP-TAG-WPRE gene fragment was ligated into the Hind III and Cla I sites of pCLHF to generate plasmid pCLHF-GFP-TAG.

The *E. coli* TyrRS gene was amplified from *E. coli* genomic DNA using the primer sequences CCACCATGGAACTC-GAGATTTTGATGGCAAGCAGTAACTTGATTAAAC (SEQ ID NO: 1) and ACAAGATCTGCTAGCTTATTTC-CAGCAAATCAGACAGTAATTC (SEQ ID NO: 2). Genes for Ome-TyrRS (Y37T, D182T, and F183M) and Bpa-TyrRS (Y37G, D182G, and L186A) were made from *E. coli* TyrRS gene through site-directed mutagenesis using overlapping PCR. The gene for EctRNA$_{CUA}^{Tyr}$ in construct tRNA2 was amplified using the primer sequences GTGGGATCCCCG-GTGGGGTTCCCGAGCGGCCAAAGGGAG CAGACTCTAAATCTGCCGTCATCGACTTCG (SEQ ID NO: 3) and GATAAGCTTTTCCAAAAATGGTGGTGGG GGAAGGATTCGAACCTTCGAAGTCGAT-GACGGCAGATTTAG (SEQ ID NO: 4) through Klenow extension. Other tRNA constructs were made by PCR using tRNA2 as the template. Genes for EctRNA$_{CUA}^{Leu}$ and the mutant synthetase specific for DanAla were amplified from plasmid pLeuRSB8T252A 20 using PCR. *E. coli* LeuRS gene was amplified from *E. coli* genomic DNA using the primers GCCTCGAGAAGAGCAATACCGCCCGG (SEQ ID NO: 5) and CGCTAGCTTAGCCAACGACCAGATTGAGGAG (SEQ ID NO: 6). The H1 promoter was amplified from plasmid pSUPER (OligoEngine).

To make the tRNA/aaRS expression plasmid pEYCUA-YRS, pBluescript II KS (Stratagene) was used as the backbone for construction. The PGK promoter and the SV40 polyA signal were inserted between EcoR I and Not I sites. The *E. coli* TyrRS gene was inserted between the PGK and SV40 polyA sequences using the introduced Xho I and Nde I sites. The H1 promoter containing the Bgl II and Hind III sites at the 3' end was cloned into the EcoR I and Cla I sites. The EctRNA$_{CUA}^{Tyr}$ was then inserted between the Bgl II and Hind III sites. Finally, a gene cassette containing the SV40 promoter followed by the neomycin resistance gene and the SV40 polyA signal was amplified from pcDNA3 (Invitrogen) and inserted into the Cla I and Kpn I sites. Other tRNA/synthetase plasmids were modified from plasmid pEYCUA-YRS by swapping the synthetase gene and/or the tRNA gene, or by inserting various 3'-flanking sequences after the tRNA.

Cell Culture and Transfection

HeLa cells, HEK293T and HEK293 cells were cultured and maintained with Dulbecco's modified Eagle's medium (DMEM, Mediatech) supplemented with 10% fetal bovine serum.

For the establishment of a GFP-TAG HeLa stable cell line, 293T cells were co-transfected with the retroviral vector pCLHF-GFP-TAG and the packaging vector pCL-Ampho (Imgenex) using FuGENE 6 transfection reagent (Roche). Viruses were harvested after 48 hours and used to infect HeLa cells grown in 50% conditioned medium in the presence of 8 ng/ml hexadimethrine bromide (Sigma). From the next day on, cells were split to a very low confluence. Stably infected cells were selected with 200 ng/ml hygromycin (Invitrogen). Hygromycin (50 ng/ml) was always present in subsequent cell culture to ascertain plasmid DNA maintenance.

Hippocampi of postnatal day 0 Sprague-Dawley rats or mice were removed and treated with 2.5% trypsin (Invitrogen) for 15 minutes at 37° C. The digestion was stopped with 10 mL of DMEM containing 10% heat-inactivated fetal bovine serum. The tissue was triturated in a small volume of this solution with a fire-polished Pasteur pipette, and ~100,000 cells in 1 mL neuronal culture medium were plated per coverslip in 24-well plates. Glass coverslips were prewashed overnight in HCl followed by several rinses with 100% ethanol and flame sterilization. They were subsequently coated overnight at 37° C. with Poly-D-Lysine. Cells were plated and grown in Neurobasal-A (Invitrogen) containing 2% B-27 (Life Technologies), 1.8% HEPES, and 2 mM glutamine (Life Technologies). Half of the medium was replaced next day. For imaging, the cells cultured for 3 days were transfected with Lipofecamine 2000, changed into fresh medium with 1 mM OmeTyr or Bpa after 5 hours, and cultured for another 24 hours prior to testing.

Northern Blot Analysis

RNA was prepared from the GFP-TAG HeLa cells transfected with different tRNA/aaRS constructs using PureLink miRNA Kit (Invitrogen). The RNA was denatured, electrophoresed on 15% PAGE gel, blotted onto Hybond-N (Amersham) membrane, and crosslinked by ultraviolet fixation. $^{32}$P-labeled DNA probes specific for the EctRNA$_{CUA}^{Tyr}$ were made using Klenow extension with the primer sequences: AACCTTCGAAGTCGATGACGGCAGATT-TACAGTCTGC (SEQ ID NO: 7) and primer CCGTCTAAATGTCAGACGAGGGAAACCGGCGAG (SEQ ID NO: 8). After pre-hybridization for 4 hours in the hybridization buffer [5× sodium chloride-sodium citrate buffer, 40 mM Na$_2$HPO$_4$ (pH7.2), 7% sodium dodecylsulfate (SDS), 2×Denhardt's], membranes were hybridized with $^{32}$P-labeled cDNA probes (0.5–2×10$^7$ c.p.m./mL) in the same buffer plus 50 µg/mL salmon sperm DNA at 58° C. overnight. Hybridized membrane was sequentially washed with high stringency buffer (40 mM Na$_2$HPO$_4$, 1 mM EDTA, 1% SDS, 58° C.) twice and exposed to an X-ray film (Kodak) for 48 hours. To control the total RNA amount loaded in each lane, glyceraldehyde-3-phosphate dehydrogenase (GAPDH) transcript was used as an internal standard.

Flow Cytometry

GFP-TAG HeLa cells were transfected with plasmid DNA by lipofection 2000 according to the protocol of the vendor (Invitrogen). UAAs (1 mM) were added into the medium immediately after transfection. Cells were collected after 48 hours, washed twice, and resuspended in 1 mL of PBS containing 0.05 μg/mL propidium iodide. Samples were analyzed with a FACScan (Becton & Dickinson).

Fluorescence Microscopy

Fluorescence images were acquired on an Olympus X81 inverted microscope using a 20× objective. For the GFP channel, filters were 480/30 nm for excitation and 535/40 nm for emission. For the mCherry channel, filters were 580/20 nm for excitation and 675/130 nm for emission.

Example 2

Expression of Orthogonal tRNAs in Eukaryotic Cells

This Example demonstrates efficient expression of prokaryotic orthogonal tRNAs in mammalian cells. Although particular methods of expressing prokaryotic orthogonal tRNAs in mammalian cells are described, one of skill in the art will appreciate that similar methods can be used to express prokaryotic tRNAs in other eukaryotic cells using other pol III promoters.

One way to generate an orthogonal tRNA/synthetase pair is to import a tRNA/synthetase pair from species in a different kingdom because the cross aminoacylation between different species is often low. However, expression of functional *E. coli* tRNAs in mammalian cells is challenging. *E. coli* and mammalian cells differ significantly in tRNA transcription and processing. *E. coli* tRNAs are transcribed by the sole RNA polymerase through promoters upstream of the tRNA structural gene. The transcription of mammalian tRNA genes, however, depends principally on promoter elements within the tRNA known as the A and B box sequences, which are recognized by RNA polymerase III (pol III) and its associated factors (Galli et al., (1981) *Nature* 294, 626-631). While all *E. coli* tRNA genes encode full tRNA sequences, mammalian tRNAs have the 3'-CCA sequence added enzymatically by the tRNA nucleotidyltransferase after transcription. In addition, the 5' and 3' flanking sequences, the removal of introns, and the export from nucleus to cytoplasm also affect mammalian tRNA expression and function. Due to these differences, *E. coli* tRNAs, especially those diverge from the preserved eukaryotic A and B box sequences, are not efficiently biosynthesized or correctly processed in mammalian cells.

As demonstrated herein, a pol III promoter lacking any requirement for intragenic elements can efficiently transcribe prokaryotic tRNAs without the preserved internal A and B boxes that are present in mammalian cells. The H1 promoter, type-3 pol III promoter (which does not have any downstream transcriptional elements; Myslinski et al., (2001) Nucleic Acids Res. 29, 2502-2509), was used for this purpose. The H1 promoter drives the expression of the human H1RNA gene, and thus is of mammalian origin. The transcription initiation site of H1 promoter is well-defined, and it can be used to generate the 5' end of the tRNA without further posttranscriptional processing.

A fluorescence-based functional assay in mammalian cells was developed to identify the expression elements that can efficiently drive the transcription of *E. coli* tRNAs to generate functional tRNAs in mammalian cells (FIG. 1A). The gene for the candidate *E. coli* amber suppressor tRNA (EctRNA$_{CUA}{}^{aa}$, whose anticodon was changed to CUA to decode the amber stop codon TAG) was co-expressed with its cognate synthetase (aaRS). A TAG stop codon was introduced at a permissive site of the green fluorescent protein (GFP) gene, and this mutant GFP gene was co-expressed with the EctRNA$_{CUA}{}^{aa}$/aaRS pair in mammalian cells. In this assay, if the EctRNA$_{CUA}{}^{aa}$ is expressed and correctly processed to a functional tRNA, the synthetase aminoacylates this tRNA with the cognate amino acid. The acylated EctRNA$_{CUA}{}^{aa}$ then suppresses the TAG codon in the GFP gene, producing full-length GFP and rendering the cells fluorescent. By comparing the fluorescence intensities of cells, this method also serves as a sensitive in vivo assay for the orthogonality of the EctRNA$_{CUA}{}^{aa}$ to endogenous synthetases of host cells when the cognate *E. coli* synthetase is not expressed, and for the activity of the orthogonal EctRNA$_{CUA}{}^{aa}$ toward unnatural-amino-acid specific mutant synthetase when the mutant synthetase is expressed in place of the cognate synthetase.

The *E. coli* tyrosyl amber suppressor tRNA (EctRNA$_{CUA}{}^{aa}$) was chosen as the candidate orthogonal tRNA because it is orthogonal to yeast synthetases and suppresses the amber stop codon efficiently in yeast when coexpressed with *E. coli* TyrRS (Edwards & Schimmel, (1990) *Mol. Cell. Biol.* 10, 1633-1641). In vitro aminoacylation assays indicate that *E. coli* TyrRS does not charge eukaryotic tRNAs (Doctor & Mudd, (1963) *J. Biol. Chem.* 238, 3677-3681). For 3' end processing of the EctRNA$_{CUA}{}^{tyr}$, the 3' flanking sequence of the human tRNA$^{fMet}$ was used. The 5' and 3' flanking sequences of the human tRNA$^{fMet}$ were found to drive the functional expression of *E. coli* EctRNA$_{CUA}{}^{gln}$ (which has the A box and B box) in mammalian cells (Drabkin et al., (1996) *Mol. Cell. Biol.* 16, 907-913). To determine the importance of the 3'-CCA trinucleotide, they were included or removed in the tRNA gene, resulting in four expression cassettes (tRNA-1 to tRNA-4) (FIG. 1B). For comparison, a control plasmid tRNA-5 was made, in which the EctRNA$_{CUA}{}^{tyr}$ was placed downstream of the 5'-flanking sequence of the human tRNA$^{Tyr}$.

To accurately compare the ability of different expression cassettes to generate functional tRNAs, a clonal stable HeLa cell line was established that expressed the GFP gene with a TAG stop codon introduced at the permissive site 182 (GFP-TAG HeLa). The tRNA/aaRS expression plasmid was transfected into the stable GFP-TAG HeLa cell line, and cells were analyzed with flow cytometry after 48 hours. The total fluorescence intensity of the green fluorescent cells indicated the amount of GFP produced, and is shown in FIG. 1C.

When no EctRNA$_{CUA}{}^{tyr}$/TyrRS was expressed, the fluorescence intensity of the GFP-TAG HeLa cell line was similar to that of HeLa cells, indicating the background read through of the TAG codon in GFP is negligible. Using the 5'-flanking sequence of human tRNA$^{Tyr}$ in tRNA-5, only weak amber suppression was detected, confirming that bacterial tRNAs without the preserved A and B boxes could not be functionally expressed in mammalian cells. The highest fluorescence intensity was found in cells transfected with tRNA-4, which was 71-fold higher than that of tRNA-5, indicating the H1 promoter can drive the functional biosynthesis of EctRNA$_{CUA}{}^{tyr}$ much more efficiently than the 5'-flanking sequence of the human tRNA$^{Tyr}$. This also indicates that the H1 promoter can generate the correct 5'-end of the tRNA directly from the transcription initiation site without the posttranscriptional processing that is necessary for endogenously expressed tRNAs.

The intensity of cells transfected with tRNA-2 was 10% of that of cells transfected with tRNA-4, indicating that the 3'-flanking sequence of the human tRNA$^{fMet}$ also is needed for the efficient expression of the EctRNA$_{CUA}{}^{tyr}$. Functional tRNA was produced in mammalian cells transfected with tRNA-1 (21% of tRNA-4), in which the CCA trinucleotide but no 3'-flanking sequence is included, which was unexpected, since mammalian cells do not encode the CCA in the tRNA gene. However, when both the CCA trinucleotide and the 3'-flanking sequence were included in tRNA-3, the fluorescence intensity dropped dramatically to 1.3%.

Northern blotting was performed to examine the transcription levels of the EctRNA$_{CUA}^{tyr}$ expressed by different constructs in GFP-TAG HeLa cells (FIG. 1D). Very low levels of EctRNA$_{CUA}^{tyr}$ were detected using a EctRNA$_{CUA}^{tyr}$-specific probe in samples transfected with tRNA-5, tRNA-3, or tRNA-2. In contrast, in cells transfected with tRNA-4 and tRNA-1, the amounts EctRNA$_{CUA}^{tyr}$ were about 93-fold and 19-fold higher than that of tRNA-5, respectively. The Northern blot data confirmed that the EctRNA$_{CUA}^{tyr}$ was transcribed in HeLa cells, and the increase of tRNA transcription was consistent with the increase of fluorescence intensity measured by cytometry in different samples.

To examine the orthogonality of the EctRNA$_{CUA}^{tyr}$ to endogenous synthetases in HeLa cells, the *E. coli* TyrRS was removed in tRNA-4 so that only EctRNA$_{CUA}^{tyr}$ was expressed. Transfection of the resultant plasmid in the GFP-TAG HeLa cell line did not change the fluorescence intensity of the cells, demonstrating that EctRNA$_{CUA}^{tyr}$ was not aminoacylated by any synthetases in HeLa cells.

To determine whether the H1 promoter, together with the 3'-flanking sequence, can be used to express other *E. coli* tRNAs, the EctRNA$_{CUA}^{tyr}$ in tRNA-4 construct was replaced with the *E. coli* leucyl amber suppressor tRNA (Ect RNA$_{CUA}^{leu}$), and the TyrRS was replaced with the cognate leucyl-tRNA synthetase (LeuRS). When only the Ect RNA$_{CUA}^{leu}$ was expressed, no fluorescence changed was observed in the GFP-TAG HeLa cells, demonstrating that EctRNA$_{CUA}^{leu}$ is orthogonal in HeLa cells. In contrast, when the EctRNA$_{CUA}^{leu}$/LeuRS were coexpressed, the GFP-TAG HeLa cells became very bright. The total fluorescence intensity was 104% of that of cells transfected with the Ect RN$_{CUA}^{tyr}$/TyrRS pair. The EctRNA$_{CUA}^{tyr}$ does not have the conserved A box, while the EctRNA$_{CUA}^{leu}$ has no A or B box sequences.

Taken together, these results demonstrate that, regardless of the internal promoter elements, the H1 promoter can efficiently drive the expression of *E. coli* tRNAs in mammalian cells, and the transcribed tRNAs are functional for amber suppression.

Example 3

Use of Unnatural Amino Acid (UAA) Synthetase in Eukaryotes

This Example describes the use of an UAA specific synthetase in mammalian cells. Although particular methods of using orthogonal synthetases in mammalian cells are described, one of skill in the art will appreciate that similar methods can be used to express and use orthogonal synthetases in other eukaryotic cells.

Synthetases specific for a variety of UAAs have been evolved in *E. coli* and in yeast from large mutant synthetase libraries containing of >$10^9$ members (Wang & Schultz, (2004) *Angew. Chem. Int. Ed. Engl.* 44, 34-66). Similar strategies cannot be practically employed in mammalian cells and neurons because the transfection efficiencies of these cells are lower by several orders of magnitude than that of *E. coli* and yeast.

To demonstrate the feasibility of transferring the mutant synthetases evolved in yeast to mammalian cells, the *E. coli* TyrRS gene in the tRNA/aaRS expression plasmid (FIG. 1A) was replaced with the gene of Ome-TyrRS, a synthetase specific for the UAA o-methyl-L-tyrosine (OmeTyr). The resultant plasmid was transfected into the GFP-TAG HeLa cell line, and cells were grown in the presence and absence of OmeTyr. As shown in FIG. 2B, without adding OmeTyr, these cells were virtually nonfluorescent and similar to the GFP-TAG HeLa cells, indicating that the expression of the Ect RNA$_{CUA}^{tyr}$/Ome-TyrRS pair does not suppress amber codons efficiently. When OmeTyr was added, 71% of cells (normalized to total number of fluorescent cells transfected with the EctRNA$_{CUA}^{tyr}$ and wild type TyrRS) became fluorescent, indicating OmeTyr was incorporated into the GFP. The incorporation efficiency was about 41% when measured by comparing the total fluorescence intensity of these cells to the intensity of cells transfected with the EctRNA$_{CUA}^{tyr}$/TyrRS pair.

To demonstrate that the transfer strategy could be generally applied to other synthetases evolved in yeast, the BpaRS, a synthetase specific for p-benzoylphenylalanine (Bpa), was tested. When the BpaRS was coexpressed with the EctRNA$_{CUA}^{tyr}$ in the GFP-TAG HeLa cell line, 47% of cells were fluorescent in the presence of Bpa, and virtually no fluorescent cells ($\leq$4%) were detected in the absence of Bpa. The incorporation efficiency of this UAA was about 13%. In addition to tRNA/aaRS pairs derived from the *E. coli* tRNA$^{Tyr}$/TyrRS, a tRNA/aaRS pair derived from *E. coli* tRNALeu/LeuRS also was tested. The EctRNA$_{CUA}^{leu}$ and a mutant synthetase specific for a fluorescent UAA 2-amino-3-(5-(dimethylamino)naphthalene-1-sulfonamido)propanoic acid (DanAla; Summerer et al. (2006) *Proc. Natl. Acad. Sci. U.S.A.* 103, 9785-9789) were expressed in GFP-TAG HeLa cell line (FIG. 2C). DanAla was incorporated in 13% efficiency, and 42% of cells became fluorescent.

These results confirm that UAA specific synthetases evolved in yeast can be used in mammalian cells to express UAAs.

Example 4

Genetic Encoding of Unnatural Amino Acids (UAAs) in Neurons

This Example describes the genetic encoding of UAAs in neurons. Although particular methods of genetic encoding of UAAs in mouse hippocampal and cortical neurons are described, one of skill in the art will appreciate that similar methods can be used to genetically encode UAAs in other types of neurons, and in neurons from other mammalian species, such as humans.

First, it was confirmed that the H1 promoter and the 3'-flanking sequence identified in HeLa cells also could generate functional amber suppressor tRNAs in neurons. Mouse hippocampal neurons were transfected with two plasmids simultaneously (FIG. 3A): the reporter plasmid pCLHF-GFP-TAG encoding a mutant GFP (182TAG) gene, and the expression plasmid encoding the *E. coli* TyrRS, the EctRNA$_{CUA}^{tyr}$ driven by either the H1 promoter or the 5' flanking sequence of human tRNA$^{Tyr}$, and a red fluorescent protein, mCherry, as an internal marker for transfection. Fluorescence microscopy was used to look for red transfected cells, and then to image their green fluorescence. The presence of green fluorescence in transfected cells indicated that functional EctRNA$_{CUA}^{tyr}$ was biosynthesized to incorporate Tyr at the 182TAG position of the GFP gene. As shown in FIG. 3B, neurons transfected with the expression plasmid in which the EctRNA$_{CUA}^{tyr}$ was driven by the H1 promoter showed intense green fluorescence, whereas no green fluorescence could be detected in neurons in which the EctRNA$_{CUA}^{tyr}$ was driven by the 5' flanking sequence of the human tRNA$^{Tyr}$.

Next, it was confirmed that UAAs could be genetically encoded in neurons using the EctRNA$_{CUA}^{tyr}$ and mutant synthetases specific for different UAAs. Synthetases evolved in yeast and proven functional in HeLa cells were used. When the Ome-TyrRS was coexpressed with the EctRNA$_{CUA}^{tyr}$, transfected neurons showed no green fluorescence in the absence of the corresponding unnatural amino acid OmeTyr (FIG. 3C), indicating that the EctRNA$_{CUA}^{tyr}$ is orthogonal to endogenous synthetases in neurons. Bright green fluorescence was observed from transfected neurons only when OmeTyr was fed to the growth media. These results indicate that OmeTyr, but no common amino acid, was incorporated into GFP at the 182TAG position. The same results were obtained for the unnatural amino acid Bpa when the BpaRS was coexpressed with the EctRNA$_{CUA}^{tyr}$ (FIG. 3D). Using this approach, OmeTyr and Bpa were also genetically encoded in hippocampal and cortical neurons isolated from rats.

Example 5

Materials and Methods

This Example describes materials and methods that were used in performing Example 6. Although particular methods are described, one of skill in the art will understand that other, similar methods also can be used.

DH10B *E. coli* cells (Invitrogen, Carlsbad, Calif.) were used for cloning and DNA preparation. Phusionm high-fidelity DNA polymerase (New England Biolabs, Ipswich, Mass.) was used for polymerase chain reaction (PCR). OmeTyr was purchased from Chem-Impex, Wood Dale, Ill. DanAla was synthesized using a procedure previously described (see, for instance, Summerer et al. (2006) *Proc. Natl. Acad. Sci. U.S.A.* 103, 9785-9789). All other chemicals were purchased from Sigma-Aldrich, St. Louis, Mo.

Construction of Plasmids

All plasmids were assembled by standard cloning methods and confirmed by DNA sequencing. A plasmid containing the 2 μori, TRP1, Kan$^r$, the ColE1 ori, and multiple cloning sites (MCS) was used as the backbone to construct plasmids expressing tRNA and synthetase. To separate the tRNA expression cassette from the synthetase expression cassette, a spacer sequence was amplified from pcDNA3 (Invitrogen, Carlsbad, Calif.) using primer FW19 (SEQ ID NO: 9) 5'-ATA CTA GTG CGG GCG CTA GGG CGC TG-3' and primer FW20 (SEQ ID NO: 10) 5'-ATG GTA CCC CTG GAA GGT GCC ACT CC-3'. This spacer was digested with Kpn I and Spe I, and inserted at the Kpn I and Xba I site of the backbone plasmid to make plasmid p-Xd. The *E. coli* TyrRS gene was amplified from *E. coli* genomic DNA using primer FW21 (SEQ ID NO: 11) 5'-CAA CTA GTA TGG AGA TTT GA TGG CAA GC-3' and primer FW22 (SEQ ID NO: 12) 5'-AAC TCG AGT TAT TTC CAG CAA ATC AGA CAG-3'. The PCR product was digested with Spe I and Xho I and ligated into the precut vector p415 (American Type Culture Collection, Manassas, Va.) to make p415-EY. The gene cassette containing the GPD promoter, the *E. coli* TyrRS gene, and the CYC1 terminator was cut from p415-EY with Sac I and Kpn I, and inserted into plasmid p-Xd to make plasmid p-TyrRS.

The SNR52 promoter was amplified from yeast genomic DNA using primer FW16 (SEQ ID NO: 13) 5'-CAC TGC AGT CTT TGA AAA GAT AAT GTA TGA TTA TG-3' and primer FW17 (SEQ ID NO: 14) 5'-GGC CGC TCG GGA ACC CCA CCG ATC ATT TAT CTT TCA CTG CGG AG-3'. The EctRNA$_{CUA}^{Tyr}$ gene followed by the 3'-flanking sequence of the SUP4 suppressor tRNA was amplified from pEYCUA-YRS (Wang et al., (2007) *Nat. Neurosci.* 10, 1063-1072) using primer FW14 (SEQ ID NO: 15) 5'-GGT GGG GTT CCC GAG CGG CCA AAG-3' and primer FW15 (SEQ ID NO: 16) 5'-GGT CGA CAG ACA TAA AAA ACA AAA AAA TGG TGG GGG AAG GAT TCG AAC CTT C-3'. These two PCR fragments were pieced together through overlapping PCR to make the SNR52-EctRNA$_{CUA}^{Tyr}$, -3' flanking sequence cassette. This tRNA expression cassette was digested with Pst I and Sal I, and ligated into the precut p-TyrRS to make pSNR-TyrRS.

The RPR1 promoter was amplified from yeast genomic DNA using primer FW12 (SEQ ID NO: 17) 5'-CAC TGC AGT CTG CCA ATT GAA CAT AAC ATG G-3' and primer FW13 (SEQ ID NO: 18) 5'-GGC CGC TCG GGA ACC CCA CCT GCC AAT CGC AGC TCC CAG AGT TTC-3'. It was pieced with the above EctRNA$_{CUA}^{Tyr}$-3' flanking sequence through overlapping PCR to make the RPR1-EctRNA$_{CUA}^{Tyr}$-3' flanking sequence cassette. The cassette was digested with Pst I and Sal I, and ligated into the precut p-TyrRS to make pRPR-TyrRS.

The gene cassette containing the 5' flanking sequence of the SUP4 suppressor tRNA, the EctRNA$_{CUA}^{Tyr}$, and the 3' flanking sequence of the SUP4 suppressor tRNA was amplified from plasmid pEYCUA-YRS-tRNA-5 (Wang et al., (2007) *Nat. Neurosci.* 10, 1063-1072) using primer (SEQ ID NO: 19) 5'-CAC TGC AGC TCT TTT TCA ATT GTA ATG TGT TAT G-3' and primer FW15. The cassette was digested with Pst I and Sal I, and ligated into the precut p-TyrRS to make pFS-TyrRS.

The OmeRS gene was made from *E. coli* TyrRS gene through site-directed mutagenesis to introduce the following mutations: Y37T, D182T, and F183M. The OmeRS gene was digested with Spe I and Xho I, and ligated into the precut pSNR-TyrRS to make pSNR-OmeRS.

The gene cassette containing the 5' flanking sequence of the SUP4 suppressor tRNA, the EctRNA$_{CUA}^{Leu}$, and the 3' flanking sequence of the SUP4 suppressor tRNA was amplified from plasmid pLeuRSB8T252A (Summerer et al., (2006) *Proc. Natl. Acad. Sci. U.S.A.* 103, 9785-9789) using primer FW27 (SEQ ID NO: 20) 5'-CAA AGC TTC TCT TTT TCA ATT GTA TAT GTG-3' and primer FW28 (SEQ ID NO: 21) 5'-GAG TCG ACA GAC ATA AAA AAC AAA AAA ATA C-3'. The PCR product was digested with Hind III and Sal I, and ligated into the precut pSNR-TyrRS to make ptRNA$^{Leu}$-TyrRS. The *E. coli* LeuRS gene was amplified from *E. coli* genomic DNA using primer FW29 (SEQ ID NO: 22) 5'-AGC TCG AGT TAG CCA ACG ACC AGA TTG AG-3' and FW30 (SEQ ID NO: 23) 5'-AGA CTA GTA TGC AAG AGC AAT ACC GCC CG-3'. The PCR product was digested with Spe I and Xho I, and ligated into the precut ptRNA$^{Leu}$-TyrRS to make pFS-LeuRS.

The SNR52 promoter was amplified from pSNR-TyrRS using primer FW16 and primer FW31 (SEQ ID NO: 24) 5'-CTA CCG ATT CCA CCA TCC GGG CGA TCA TTT ATC TTT CAC TGC GG-3'. The EctRNA$_{CUA}^{Leu}$-3' flanking sequence fragment was amplified from pLeuRSB8T252A using primer FW32 (SEQ ID NO: 25) 5'-GCC CGG ATG GTG GAA TCG GTA G-3' and primer FW28. These two PCR fragments were pieced together through overlapping PCR to make the gene cassette SNR52-EctRNA$_{CUA}^{Leu}$-3' flanking sequence. The gene cassette was digested with Pst I and Sal I, and ligated into the precut pSNR-TyrRS to make pSNRtRNA$^{Leu}$-TyrRS. The TyrRS gene was then replaced with the E. coli LeuRS gene using Spe I and Xho I sites to make pSNR-LeuRS.

The DanRS gene was amplified from plasmid pLeuRSB8T252A using primer FW29 and primer FW30. The PCR product was digested with Spe I and Xho I, and ligated into the precut pSNR-LeuRS to make pSNR-DanRS.

A plasmid containing the 2 μori, LEU2, Amp$^r$, the ColE1 ori, and MCS was used as the backbone to construct the GFP-TAG reporter plasmids. Site-directed mutagenesis was used to introduce Tyr39TAG and Tyr182TAG mutations into the EGFP gene. The mutant GFP-TAG gene was amplified with primer JT171 (SEQ ID NO: 26) 5'-TAG TCG GAT CCT CAG TGA TGG TGA TGG TGA TGC TTG TAC AGC TCG TCC ATG CC-3' and primer JT172 (SEQ ID NO: 27) 5'-TAG TCG TCG ACA TGG ATT ACA AAG ATG ATG ATG ATA AAG TGA GCA AGG GCG AGG AG-3' to add a His6 tag at the C-terminus and a HA tag at the N-terminus. The PCR product was then flanked by the ADH1 promoter and ADH1 terminator, and the whole gene cassette was cloned into the backbone plasmid using the Hind III and EcoR I sites to make pGFP-39TAG or pGFP-182TAG.

Northern Blot Analysis

RNA was prepared from yeast cells transformed with different tRNA expressing constructs using PureLink miRNA Isolation Kit (Invitrogen, Carlsbad, Calif.). The RNA was denatured and electrophoresed on 8% PAGE gel with 8 M urea. A large DNA sequencing gel (15 inches in length) was used to obtain high resolution. After electrophoresis, the samples were blotted onto Hybond-N+ (Amersham Biosciences, Uppsala, Sweden) membrane, and crosslinked by ultraviolet fixation. The membrane was hybridized overnight at 55° C. with a biotinylated probe FW39 (SEQ ID NO: 28) 5'-TCT GCT CCC TTT GGC CGC TCG GGA ACC CC-biotin-3', which is specific for the E. coli tRNA$^{Tyr}$ and the EctRNA$_{CUA}^{Tyr}$. The hybridized probe was detected using the North2South® chemiluminescent hybridization and detection kit (Pierce Biotechnology, Inc., Rockford, Ill.) according to the manufacturer's protocol. The amount of cell pellet was used to control the total RNA loaded in each lane.

Flow Cytometry

A single yeast clone was selected and cultured in 5 mL liquid medium at 30° C. for 48 hours. These cells were used to inoculate 10 mL of fresh medium with a starting OD$_{600}$ of 0.2. Cells were grown at 30° C. in an orbital shaker (250 rpm) for 6 hours. Cells were then pelleted, washed once with PBS, and resuspended in PBS. Samples were analyzed with a FACScanm (Becton & Dickinson, Franklin Lakes, N.J.).

Generation of the upf1 Δ Strain

A gene cassette containing ~200 bp upstream of UPF1, the Kan-MX6, and ~200 bp downstream of UPF1 was made using primer FW5 (SEQ ID NO: 29) 5'-AAT GAA AAG CTT ACC AGA AAC TTA CG-3' and primer FW6 (SEQ ID NO: 30) 5'-GGC TAG GAT ATC AAG TCC ATG CC-3'. The PCR product was transformed into yeast strain YVL2968 (MATA α ura3-52 lys2-801 trpΔ1 his3Δ200 leu2Δ1) using the lithium acetate method. Transformed cells were plated on G418 YPAD plates for selection. The genomic DNA of surviving clones were amplified with primers ~300 bp away from the UPF1 gene (FORWARD (SEQ ID NO: 31) 5'-GAT TTG GGA GGG ACA CCT TTA TAC GC-3', REVERSE (SEQ ID NO: 32) 5'-TTC ATT AGA AGT ACA ATG GTA GCC C-3'), and the PCR products were sequenced to confirm that the UPF1 gene was replaced with the Kan-MX6 through homologous recombination. The resultant upf1 Δ strain was designated as LWUPF1Δ. YVL2968 is a wild type, protease-proficient haploid strain that is derived from S288C, and it was used as the wild type strain in all of Example 6.

Protein Expression and Purification

Yeast culture (5 mL) was started from a single clone and grown for 48 hours. These cells were used to inoculate 200 mL fresh medium with or without 1 mM DanAla. After incubating at 30° C. for 48 hours, cells were pelleted and lysed with Y-PER (Pierce Biotechnology, Inc., Rockford, Ill.) in the presence of EDTA-free protease inhibitor (Roche, Basel, Switzerland). After agitating at room temperature for 20 minutes, the mixture was sonicated for 1 minute using a Sonic Dismembrator (Fisher Scientific, Pittsburgh, Pa.). After centrifugation, a second Y-PER extraction and sonication was applied to the pellet. Cleared cell lysates were combined and incubated with 2 mL Ni-NTA slurry (Qiagen, Hilden, Germany) for 1 hour at 4° C. The column was washed with 10 bed volumes of PBS buffer (pH7.5, 140 mM NaCl) followed by 10 bed volumes of washing buffer (PBS pH7.5, 140 mM NaCl, 20 mM imidazole). The His6-tagged GFP protein was eluted with the elution buffer (PBS pH7.5, 140 mM NaCl, 250 mM imidazole), and exchanged into the PBS buffer using Amicon Centricon™ concentrators (Millipore, Billerica, Mass.). Protein concentration was determined by the Bradford assay (Bio-Rad, Hercules, Calif.).

Western Blot Analysis

Wild type EGFP with a His6 tag at the C-terminus and a HA tag at the N-terminus was purified and used as the positive control. The same amounts of yeast cells from each sample were lysed with Y-PER in the presence of EDTA-free protease inhibitor. After centrifugation at 14,000 g for 10 minutes, 5 μl of the supernatants were loaded and separated by SDS-PAGE. A monoclonal penta H is antibody (Invitrogen, Carlsbad, Calif.) was used to detect the His6-containing proteins.

Example 6

De-Activation of the NMD Pathway Increases UAA Incorporation Efficiency

This Example describes methods of improving the efficiency of methods of incorporation of unnatural amino acids. Although the results described below are demonstrate increased UAA incorporation efficiency when used with orthogonal tRNA/synthetase pairs and a pol III promoter, the efficiency of any strategy for the incorporation of UAAs (for instance, using a 5' flanking sequence methodology) is improved by de-activation of the NMD pathway in a eukaryotic cell in which the UAA is expressed, as described herein As described above in the foregoing Examples, unnatural amino acids (UAAs) with novel chemical and physical properties have been genetically encoded in cells by using orthogonal tRNA-codon-synthetase sets. However, in some embodiments the UAA incorporation efficiency is further improved or optimized. For instance, although tens of miligrams of UAA-containing proteins were produced from 1 liter of E. coli culture, in some embodiments, the yield in yeast is only tens of micrograms.

It is particularly challenging to express orthogonal bacterial tRNAs in yeast, because yeast and bacterium differ significantly in tRNA transcription and processing. Bacterial tRNAs expressed in yeast using the conventional method are not competent in translation, thus, as described herein, a new method was developed to express different orthogonal bacterial tRNAs in yeast with high activity. In addition, mRNA stability of the target gene is a unique, unaddressed issue for UAA incorporation in yeast. The Nonsense-Mediated mRNA Decay (NMD) pathway mediates the rapid degradation of mRNAs that contain premature stop codons in yeast, whereas no such pathway exists in *E. coli*. When stop codons are used to encode UAAs, in some examples NMD results in a shorter lifetime for the target mRNA, and thus a lower protein yield in yeast. An NMD-deficient yeast strain was generated, and, as disclosed herein, this strain indeed increased the UAA incorporation efficiency in comparison to the wild-type (wt) yeast. These strategies enabled UAAs to be incorporated into proteins in yeast in high yields of tens of miligrams per liter.

This strategy also can be used effectively in mammalian cells. In mammalian cells, the efficacy of disrupting the NMD pathway depends on the presence of exon-intron junctions in the DNA sequence. Thus, if there are introns in the gene encoding the UAA of interest, disrupting the NMD pathway increases the efficiency of UAA incorporation.

*E. coli* tRNAs are transcribed by the sole RNA polymerase (Pol) through promoters upstream of the tRNA gene. However, the transcription of yeast tRNAs by Pol III depends principally on promoter elements within the tRNA known as the A- and B-box (FIG. 4A). The A- and B-box identity elements are conserved among eukaryotic tRNAs, but are lacking in many *E. coli* tRNAs. Creating the consensus A- and B-box sequences in *E. coli* tRNAs through mutation could cripple the tRNA, as these nucleotides make up the conserved tertiary base pairs bridging the tRNA D- and T-loop. In addition, all *E. coli* tRNA genes encode full tRNA sequences, whereas yeast tRNAs have the 3'-CCA trinucleotide enzymatically added after transcription. Therefore, transplanting *E. coli* tRNA into the tRNA gene cassette in yeast does not generate functional tRNA.

However, as disclosed herein, *E. coli* tRNAs are expressed efficiently in yeast using the following strategy: a promoter containing the consensus A- and B-box sequences is placed upstream of the *E. coli* tRNA to drive transcription, and is cleaved post-transcriptionally to yield the mature tRNA (FIG. 4B). Two internal leader promoters, SNR52 and RPR1, share a promoter organization consisting of a leader sequence in which the A- and B-boxes are internal to the primary transcript but are external to the mature RNA product. It is shown herein that the SNR52 and RPR1 promoter can be exploited to express *E. coli* tRNAs in yeast.

The gene for *E. coli* tyrosyl amber suppressor tRNA (EctRNA$_{CUA}^{Tyr}$) lacking the 3'-CCA trinucleotide was placed after the candidate promoter and followed by the 3'-flanking sequence of the yeast tRNA SUP4 (FIG. 4C). This tRNA gene cassette was coexpressed with the cognate *E. coli* tyrosyl-tRNA synthetase (TyrRS) in *S. cerevisiae*. An in vivo fluorescence assay was developed to test whether the expressed EctRNA$_{CUA}^{Tyr}$ is functional for protein translation in yeast. A TAG stop codon was introduced at a permissive site (Tyr39) of the green fluorescent protein (GFP) gene, and this mutant gene is coexpressed with the EctRNA$_{CUA}^{Tyr}$/TyrRS. If the EctRNA$_{CUA}^{Tyr}$ is transcribed and correctly processed into a functional tRNA, the TyrRS will aminoacylate it with tyrosine, and the acylated EctRNA$_{CUA}^{Tyr}$ will then suppress the TAG codon, producing full-length GFP and rendering cells fluorescent. The fluorescence intensities of cells indicate how efficiently a promoter can drive the functional expression of the EctRNA$_{CUA}^{Tyr}$ in yeast. When the EctRNA$_{CUA}^{Tyr}$ was expressed using the conventional method, the 5'-flanking sequence of an endogenous yeast tRNA SUP4, weak fluorescence could be detected, confirming that the 5'-flanking sequence expressed functional EctRNA$_{CUA}^{Tyr}$ with low efficiency only (FIG. 4D). In contrast, when the EctRNA$_{CUA}^{Tyr}$ was driven by the SNR52 or RPR1 promoter, cells showed strong fluorescence, the mean intensities of which were increased 9- and 6-fold, respectively, in comparison to cells containing the 5'-flanking sequence. These results indicate that both the SNR52 and RPR1 promoter can drive the EctRNA$_{CUA}^{Tyr}$ expression in yeast efficiently, and the expressed EctRNA$_{CUA}^{Tyr}$ is functional in translation.

The transcription levels of the EctRNA$_{CUA}^{Tyr}$ driven by different promoters were measured by Northern blot. Unexpectedly, the 5'-flanking sequence of SUP4 generated ~100 fold more EctRNA$_{CUA}^{Tyr}$ than the SNR52 or RPR1 promoter (FIG. 4E). The fact that these EctRNA$_{CUA}^{Tyr}$ were much less active in protein translation than those expressed by the SNR52 or RPR1 promoter indicates that the EctRNA$_{CUA}^{Tyr}$ expressed by the 5'-flanking sequence is not correctly processed or modified. Indeed, the heterogeneity of the EctRNA$_{CUA}^{Tyr}$ expressed by the 5'-flanking sequence was evident by multiple bands, which did not exist in the other two samples.

To determine whether this method can be generally used to express other *E. coli* tRNAs, the EctRNA$_{CUA}^{Tyr}$ were replaced with the *E. coli* leucyl amber suppress tRNA (EctRNA$_{CUA}^{Leu}$ and the TyrRS with the *E. coli* leucyl-tRNA synthetase (LeuRS). The 5'-flanking sequence of SUP4 could also drive the EctRNA$_{CUA}^{Leu}$ expression in yeast, but the fluorescence intensity increased 4-fold when the SNR52 promoter was used (FIG. 4D). According to the yeast A- and B-box identity elements, the EctRNA$_{CUA}^{Tyr}$ does not have a fully matched A-box, while the EctRNA$_{CUA}^{Leu}$ has matched A- and B-box. Regardless of the identity elements, the SNR52 promoter significantly increased the functional expression of both types of *E. coli* tRNAs in yeast.

Next, the effect of NMD inactivation on the UAA incorporation efficiency was examined in yeast. The amber stop codon TAG is the most frequently used to encode UAAs, but mRNAs containing premature stop codons are rapidly degraded in yeast by the NMD pathway, a surveillance mechanism to prevent the synthesis of truncated proteins. Inactivation of NMD preserved the stability of the UAG-containing target mRNA and thus enhanced the incorporation efficiency of UAAs. The yeast UPF1 gene has been shown to be essential for NMD, deletion of which restores wild-type decay rates to nonsense-containing mRNA transcripts. Therefore, a upf1 Δ strain of *S. cerevisiae* was generated, and the UAA incorporation efficiency was compared in this strain to the wild-type strain.

The EctRNA$_{CUA}^{Leu}$ driven by the SNR52 promoter and the DanRS11 were used to incorporate the fluorescent UAA DanAla (FIG. 5C) into the GFP at site 39. When DanAla was added to the growth media, the fluorescence intensity of the upf1 Δ strain was doubled compared to that of the wt strain (FIG. 5A). In the absence of DanAla, the intensities dropped to low background levels, suggesting high specificity of the EctRNA$_{CUA}^{Leu}$/DanRS pair for DanAla. The incorporation of UAA OmeTyr also was tested using the EctRNA$_{CUA}^{Leu}$/OmeRS pair. When OmeTyr was added, the fluorescence intensity of the upf1Δ strain was also increased twofold compared to the wild-type strain. However, in the absence of OmeTyr, the fluorescence intensities in both strains were still quite high. The EctRNA$_{CUA}^{Tyr}$ only were then expressed, without the OmeRS, and cell fluorescence intensities dropped down to the background. This result shows that the OmeRS still charges natural amino acids to the EctRNA$_{CUA}^{Tyr}$, consistent with the mass spectrometric analysis, in which ~7% of the incorporated amino acids were found to be natural ones. The upf1 Δ strain with the GFP-TAG reporter thus also provides a sensitive assay for the specificity of evolved synthetases toward the UAA.

To examine how the above improvements correlate with protein yield, the GFP(39TAG) gene was expressed in the upf1 Δ strain using the DanRS and the EctRNA$_{CUA}^{Leu}$ was driven by the SNR52 promoter (FIG. 5B). In the presence of 1 mM DanAla, the full-length GFP was produced in an overall purified yield of 15±2 mg/l, about 300-fold higher than the previous system and comparable to the yield in E. coli.

These results demonstrate a new method for expressing orthogonal bacterial tRNA in yeast, which is general for various tRNAs and produces tRNAs highly competent in translation. These new approaches dramatically improved the yield of UAA-containing proteins in yeast. In addition, orthogonal tRNA/synthetase pairs evolved in yeast have been used to genetically encode UAAs in mammalian cells.

Example 7

Using Orthogonal tRNA/Synthetase Pairs to Express Unnatural Amino Acids in Eukaryotic Cells This Example demonstrates expression in eukaryotic cells of a prokaryotic orthogonal tRNA, together with an unnatural-amino-acid specific synthetase, in order to express unnatural amino acids in the eukaryotic cells. Although particular methods are described, one of skill in the art will appreciate that other similar methods can be used to express unnatural amino acids in eukaryotic cells.

A tRNA/synthetase pair is selected that will be orthogonal to the eukaryotic cell in which expression of the unnatural amino acid is desirable. One way to identify a tRNA/synthetase pair that will be orthogonal to the eukaryotic cell is to select a tRNA/synthetase pair from species in a different kingdom, for example a prokaryotic tRNA/synthetase pair, since the cross aminoacylation between different species often is low. An orthogonal tRNA/synthetase pair will exhibit little or no crosstalk with endogenous eukaryotic tRNA/synthetase pairs.

A promoter also is chosen that will drive expression of the tRNA. Expression of functional prokaryotic tRNAs in mammalian cells can be difficult because of the different tRNA transcription and processing involved in prokaryotes and eukaryotes. However, a pol III that lacks any requirement for intragenic elements can efficiently transcribe prokaryotic tRNAs in eukaryotic cells. Different pol III polymerases are chosen depending on the type of eukaryotic cell and the prokaryotic tRNA to be expressed. In some embodiments, the pol III promoter is a type-3 promoter. Specific non-limiting examples of promoters of use include the H1 promoter, as well as the promoters for U6 snRNA, 7SK, and MRP/7-2. A promoter also is selected that will drive expression of the synthetase. Numerous promoters will accomplish this goal. One specific, non-limiting example is a PGK promoter.

In some examples, for high-efficiency incorporation of UAA in yeast, an internal leader promoter is selected. Certain Pol III type 3 promoters from yeast (e.g., internal leader promoters), are transcribed together with the tRNA, and are then cleaved post-transcriptionally to yield the tRNA. Specific, non-limiting examples of internal leader promoters include the SNR52 promoter and the RPR1 promoter.

The tRNA chosen is one that recognizes a suppressor codon, such as a stop codon or an extended codon, for example amber, ochre, or opal. The synthetase chosen is specific for an unnatural amino acid. One or more vectors (such as an expression plasmid or viral vector) are selected for transforming the eukaryotic cell with the tRNA and the synthetase. The pol III promoter is inserted upstream of the tRNA gene using standard molecular biology techniques, the promoter that will drive expression of the synthetase is inserted upstream of the synthetase gene in the same or a different vector. The eukaryotic cell is then transformed with the vector(s) using conventional techniques.

A source of the unnatural amino acid is provided to the transformed cell, for example in the cell culture medium. When the eukaryotic cell expresses both the prokaryotic tRNA and synthetase, the synthetase charges the tRNA with the unnatural amino acid, the tRNA recognizes the stop or extended codon, and the unnatural amino acid is inserted into peptide.

Example 8

Use of Unnatural Amino Acid (UAA) Synthetase in Stem Cells

This Example describes the use of an UAA specific synthetase in stem cells. Although particular methods of using orthogonal synthetases in stem cells are described, one of skill in the art will appreciate that similar methods can be used for other stem cells and other UAAs.

Figure 6B:
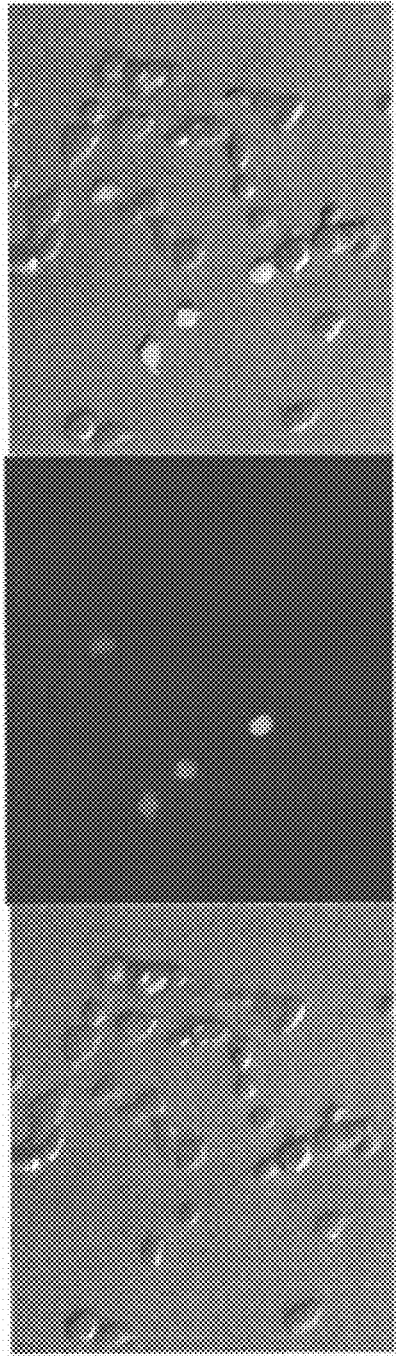
FIG. 6B shows that the H1 promoter drives *E. coli* tRNA$^{Tyr}$, and the OmeRS, a synthetase specific for the UAA o-methyl-tyrosine, incorporates this UAA into GFP.

It was confirmed that the H1 promoter and the 3'-flanking sequence identified in HeLa cells also can generate functional amber suppressor tRNAs in neural stem cells. HCN-A94 cells were transfected with two plasmids simultaneously (FIG. 6): the reporter plasmid pCLHF-GFP-TAG encoding a mutant GFP (182TAG) gene, and the expression plasmid encoding the E. coli TyrRS, the EctRNA$_{CUA}^{tyr}$ driven by either the H1 promoter or the 5' flanking sequence of human tRNA$^{Tyr}$. Fluorescence microscopy was used to image green fluorescence. The presence of green fluorescence in transfected cells indicated that functional EctRNA$_{CUA}^{tyr}$ was biosynthesized to incorporate Tyr at the 182TAG position of the GFP gene. As shown in FIG. 6A, HCN cells transfected with the expression plasmid in which the EctRNA$_{CUA}^{tyr}$ was driven by the H1 promoter showed intense green fluorescence, whereas no green fluorescence could be detected in neurons in which the EctRNA$_{CUA}^{tyr}$ was driven by the 5' flanking sequence of the human tRNA$^{tyr}$.

Figure 7A:
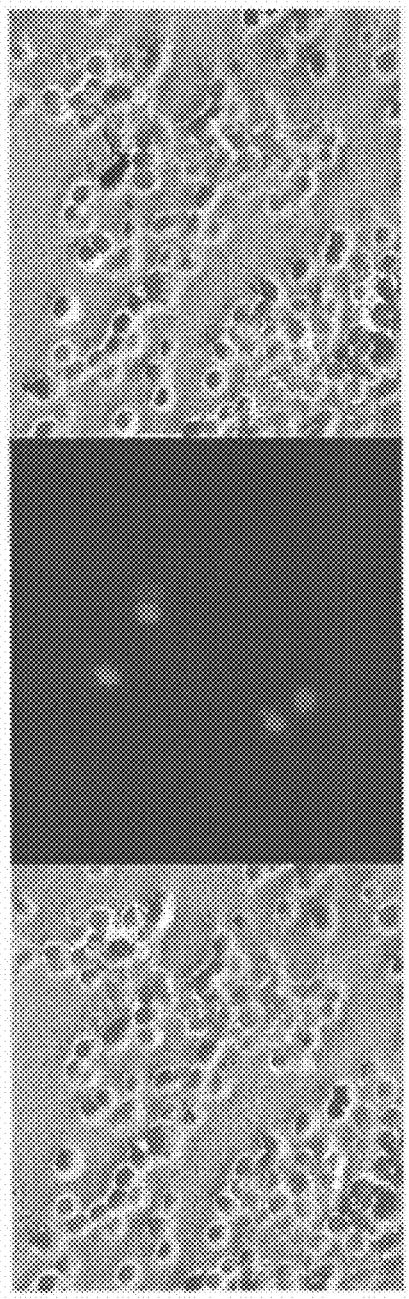
FIG. 7A shows that the H1 promoter driven *E. coli* tRNA$^{Tyr}$ and the BpaRS, a synthetase specific for the UAA p-benzoylphenylalanine, incorporate this UAA into GFP.
Figure 7B:
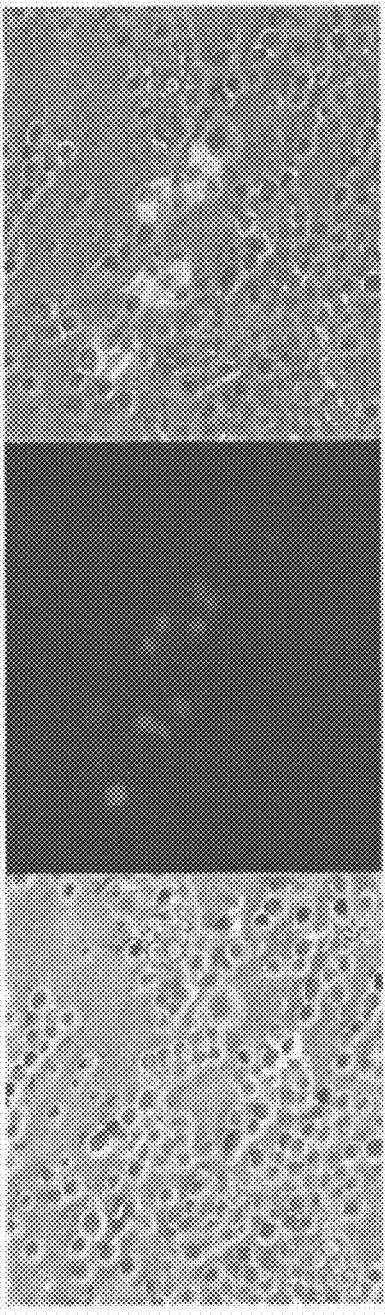
FIG. 7B shows that the H1 promoter can express the orthogonal *E. coli* tRNAL$^{Leu}$ in HCN cells. Together with the orthogonal Dansyl-RS, the tRNA$^{Tyr}$ incorporates the UAA dansylalanine into the GFP.

Next, it was confirmed that UAAs could be genetically encoded in stem cells using the EctRNA$_{CUA}^{tyr}$ and mutant synthetases specific for different UAAs. Synthetases evolved in yeast and proven functional in HeLa cells were used. When the Ome-TyrRS was coexpressed with the EctRNA$_{CUA}^{tyr}$, transfected stem cells showed no green fluorescence in the absence of the corresponding unnatural amino acid OmeTyr (FIG. 6B), indicating that the EctRNA$_{CUA}^{tyr}$ is orthogonal to endogenous synthetases in HCN stem cells. Bright green fluorescence was observed from transfected stem cells only when OmeTyr was fed to the growth media. These results indicate that OmeTyr, but no common amino acid, was incorporated into GFP at the 182TAG position. The same results were obtained for the unnatural amino acid Bpa when the BpaRS was coexpressed with the EctRNA$_{CUA}^{tyr}$ (FIG. 7A), and for the unnatural amino acid dansylalanine when the Dansyl-RS was coexpressed with the EctRNA$_{CUA}^{tyr}$.

These results confirm that UAA specific synthetases evolved in yeast can be used in stem cells to express UAAs.

While this disclosure has been described with an emphasis upon particular embodiments, it will be obvious to those of ordinary skill in the art that variations of the particular embodiments can be used and it is intended that the disclosure can be practiced otherwise than as specifically described herein. Accordingly, this disclosure includes all modifications encompassed within the spirit and scope of the disclosure as defined by the following claims:

SEQUENCE LISTING

<160> NUMBER OF SEQ ID NOS: 34

<210> SEQ ID NO 1
<211> LENGTH: 48
<212> TYPE: DNA
<213> ORGANISM: Artificial Sequence
<220> FEATURE:
<223> OTHER INFORMATION: forward primer sequences used to amplify the E.
      coli TyrRS gene

<400> SEQUENCE: 1
ccaccatgga actcgagatt ttgatggcaa gcagtaactt gattaaac                48

<210> SEQ ID NO 2
<211> LENGTH: 43
<212> TYPE: DNA
<213> ORGANISM: Artificial Sequence
<220> FEATURE:
<223> OTHER INFORMATION: reverse primer sequences used to amplify the E.
      coli TyrRS gene

<400> SEQUENCE: 2
acaagatctg ctagcttatt tccagcaaat cagacagtaa ttc                    43

<210> SEQ ID NO 3
<211> LENGTH: 69
<212> TYPE: DNA
<213> ORGANISM: Artificial Sequence
<220> FEATURE:
<223> OTHER INFORMATION: forward primer sequence used to amplify the
      gene for EctRNATyr in construct tRNA2

<400> SEQUENCE: 3
gtgggatccc cggtggggtt cccgagcggc caaagggagc agactctaaa tctgccgtca    60
tcgacttcg                                                           69

<210> SEQ ID NO 4
<211> LENGTH: 69
<212> TYPE: DNA
<213> ORGANISM: Artificial Sequence
<220> FEATURE:
<223> OTHER INFORMATION: reverse primer sequence used to amplify the
      gene for EctRNATyr in construct tRNA2

<400> SEQUENCE: 4
gataagcttt tccaaaaatg gtggtgggggg aaggattcga accttcgaag tcgatgacgg    60
cagatttag                                                           69

<210> SEQ ID NO 5
<211> LENGTH: 26
<212> TYPE: DNA
<213> ORGANISM: Artificial Sequence
<220> FEATURE:
<223> OTHER INFORMATION: forward primer sequence used to amplify the
      gene for the E. coli LeuRS gene

<400> SEQUENCE: 5
gcctcgagaa gagcaatacc gcccgg                                        26

<210> SEQ ID NO 6
<211> LENGTH: 31
<212> TYPE: DNA
<213> ORGANISM: Artificial Sequence
<220> FEATURE:
<223> OTHER INFORMATION: reverse primer sequence used to amplify the gene for the E. coli LeuRS gene

<400> SEQUENCE: 6
cgctagctta gccaacgacc agattgagga g                                31

<210> SEQ ID NO 7
<211> LENGTH: 37
<212> TYPE: DNA
<213> ORGANISM: Artificial Sequence
<220> FEATURE:
<223> OTHER INFORMATION: forward primer sequence used to amplify the
      gene for 32P-labeled DNA probes specific for the EctRNATyr

<400> SEQUENCE: 7
aaccttcgaa gtcgatgacg gcagatttac agtctgc                          37

<210> SEQ ID NO 8
<211> LENGTH: 33
<212> TYPE: DNA
<213> ORGANISM: Artificial Sequence
<220> FEATURE:
<223> OTHER INFORMATION: reverse primer sequence used to amplify the
      gene for 32P-labeled DNA probes specific for the EctRNATyr

<400> SEQUENCE: 8
ccgtctaaat gtcagacgag ggaaaccggc gag                              33

<210> SEQ ID NO 9
<211> LENGTH: 26
<212> TYPE: DNA
<213> ORGANISM: Artificial Sequence
<220> FEATURE:
<223> OTHER INFORMATION: forward sequence FW19 used to amplify a spacer
      sequence from pCDNA3

<400> SEQUENCE: 9
atactagtgc gggcgctagg gcgctg                                      26

<210> SEQ ID NO 10
<211> LENGTH: 26
<212> TYPE: DNA
<213> ORGANISM: Artificial Sequence
<220> FEATURE:
<223> OTHER INFORMATION: reverse primer sequence FW20 used to amplify a
      spacer sequence from pCDNA3

<400> SEQUENCE: 10
atggtacccc tggaaggtgc cactcc                                      26

<210> SEQ ID NO 11
<211> LENGTH: 27
<212> TYPE: DNA
<213> ORGANISM: Artificial Sequence
<220> FEATURE:
<223> OTHER INFORMATION: forward primer sequence FW21 used to amplify
      the E. coli TyrRS gene from E. coli genomic DNA

<400> SEQUENCE: 11
caactagtat ggagattttg atggcaa                                     27

<210> SEQ ID NO 12
<211> LENGTH: 30
<212> TYPE: DNA
<213> ORGANISM: Artificial Sequence
<220> FEATURE:
<223> OTHER INFORMATION: reverse primer sequence FW22 used to amplify
      the E. coli TyrRS gene from E. coli genomic DNA -continued

```
<400> SEQUENCE: 12
aactcgagtt atttccagca aatcagacag                                     30

<210> SEQ ID NO 13
<211> LENGTH: 35
<212> TYPE: DNA
<213> ORGANISM: Artificial Sequence
<220> FEATURE:
<223> OTHER INFORMATION: forward primer sequence FW16 used to amplify
      the SNR52 promoter from yeast genomic DNA

<400> SEQUENCE: 13
cactgcagtc tttgaaaaga taatgtatga ttatg                               35

<210> SEQ ID NO 14
<211> LENGTH: 44
<212> TYPE: DNA
<213> ORGANISM: Artificial Sequence
<220> FEATURE:
<223> OTHER INFORMATION: reverse primer sequence FW17 used to amplify
      the SNR52 promoter from yeast genomic DNA

<400> SEQUENCE: 14
ggccgctcgg gaaccccacc gatcatttat ctttcactgc ggag                     44

<210> SEQ ID NO 15
<211> LENGTH: 24
<212> TYPE: DNA
<213> ORGANISM: Artificial Sequence
<220> FEATURE:
<223> OTHER INFORMATION: forward primer sequence FW14  used to amplify
      the EctRNATyr gene followed by the 3'-flanking sequence of the
      SUP4 suppressor tRNA from pEYCUA-YRS

<400> SEQUENCE: 15
ggtggggttc ccgagcggcc aaag                                           24

<210> SEQ ID NO 16
<211> LENGTH: 52
<212> TYPE: DNA
<213> ORGANISM: Artificial Sequence
<220> FEATURE:
<223> OTHER INFORMATION: reverse primer sequence FW15 used to amplify
      the EctRNATyr gene followed by the 3'-flanking sequence of the
      SUP4 suppressor tRNA from pEYCUA-YRS

<400> SEQUENCE: 16
ggtcgacaga cataaaaaac aaaaaaatgg tggggaagg attcgaacct tc              52

<210> SEQ ID NO 17
<211> LENGTH: 31
<212> TYPE: DNA
<213> ORGANISM: Artificial Sequence
<220> FEATURE:
<223> OTHER INFORMATION: forward sequence FW12 used to amplify the RPR1
      promoter from yeast genomic DNA

<400> SEQUENCE: 17
cactgcagtc tgccaattga acataacatg g                                   31

<210> SEQ ID NO 18
<211> LENGTH: 45
<212> TYPE: DNA
<213> ORGANISM: Artificial Sequence
<220> FEATURE:
<223> OTHER INFORMATION: reverse primer sequence FW13 used to amplify
      the RPR1 promoter from yeast genomic DNA
```

-continued

```
<400> SEQUENCE: 18
ggccgctcgg gaaccccacc tgccaatcgc agctcccaga gtttc                    45

<210> SEQ ID NO 19
<211> LENGTH: 34
<212> TYPE: DNA
<213> ORGANISM: Artificial Sequence
<220> FEATURE:
<223> OTHER INFORMATION: forward primer sequence used to amplify a gene
      cassette containing the 5' flanking sequence of the SUP4
      suppressor tRNA, the EctRNATyr, and the 3' flanking sequence of
      the SUP4 suppressor tRNA from plasmid pEYCUA-YRS-tRNA-5

<400> SEQUENCE: 19
cactgcagct cttttcaat tgtaatgtgt tatg                                 34

<210> SEQ ID NO 20
<211> LENGTH: 30
<212> TYPE: DNA
<213> ORGANISM: Artificial Sequence
<220> FEATURE:
<223> OTHER INFORMATION: forward primer sequence FW27 used to amplify a
      gene cassette containing the 5' flanking sequence of the SUP4
      suppressor tRNA, the EctRNALeu, and the 3' flanking sequence of
      the SUP4 suppressor tRNA from plasmid pLeuRSB8T252A

<400> SEQUENCE: 20
caaagcttct cttttcaat tgtatatgtg                                      30

<210> SEQ ID NO 21
<211> LENGTH: 31
<212> TYPE: DNA
<213> ORGANISM: Artificial Sequence
<220> FEATURE:
<223> OTHER INFORMATION: reverse primer sequenc3 FW28 used to amplify a
      gene cassette containing the 5' flanking sequence of the SUP4
      suppressor tRNA, the EctLeu, and the 3' flanking sequence of the
      SUP4 suppressor tRNA from plasmid pLeuRSB8T252A

<400> SEQUENCE: 21
gagtcgacag acataaaaaa caaaaaaata c                                   31

<210> SEQ ID NO 22
<211> LENGTH: 29
<212> TYPE: DNA
<213> ORGANISM: Artificial Sequence
<220> FEATURE:
<223> OTHER INFORMATION: forward primer sequence FW29 used to amplify
      the E. coli LeuRS gene from E. coli genomic DNA

<400> SEQUENCE: 22
agctcgagtt agccaacgac cagattgag                                      29

<210> SEQ ID NO 23
<211> LENGTH: 29
<212> TYPE: DNA
<213> ORGANISM: Artificial Sequence
<220> FEATURE:
<223> OTHER INFORMATION: reverse primer sequence FW30 used to amplify
      the E. coli LeuRS gene from E. coli genomic DNA

<400> SEQUENCE: 23
agactagtat gcaagagcaa taccgcccg                                      29

<210> SEQ ID NO 24
<211> LENGTH: 44
<212> TYPE: DNA
<213> ORGANISM: Artificial Sequence
```

```
<220> FEATURE:
<223> OTHER INFORMATION: reverse primer sequence FW31 used to amplify
      the SNR52 promoter from pSNR-TyrRS

<400> SEQUENCE: 24
ctaccgattc caccatccgg gcgatcattt atctttcact gcgg                    44

<210> SEQ ID NO 25
<211> LENGTH: 22
<212> TYPE: DNA
<213> ORGANISM: Artificial Sequence
<220> FEATURE:
<223> OTHER INFORMATION: forward primer sequence FW32 used to amplify
      the EctRNALeu -3' flanking sequence fragment from pLeuRSB8T252A

<400> SEQUENCE: 25
gcccggatgg tggaatcggt ag                                            22

<210> SEQ ID NO 26
<211> LENGTH: 53
<212> TYPE: DNA
<213> ORGANISM: Artificial Sequence
<220> FEATURE:
<223> OTHER INFORMATION: forward primer sequence JT171 used to amplify
      a mutant GFP-TAG gene

<400> SEQUENCE: 26
tagtcggatc ctcagtgatg gtgatggtga tgcttgtaca gctcgtccat gcc          53

<210> SEQ ID NO 27
<211> LENGTH: 56
<212> TYPE: DNA
<213> ORGANISM: Artificial Sequence
<220> FEATURE:
<223> OTHER INFORMATION: reverse primer sequence JT172 used to amplify a
      mutant GFP-TAG gene

<400> SEQUENCE: 27
tagtcgtcga catggattac aaagatgatg atgataaagt gagcaagggc gaggag       56

<210> SEQ ID NO 28
<211> LENGTH: 29
<212> TYPE: DNA
<213> ORGANISM: Artificial Sequence
<220> FEATURE:
<223> OTHER INFORMATION: sequence of a biotinylated probe FW39 which is
      specific for the E. coli tRNATyr and the EctRNATyr

<400> SEQUENCE: 28
tctgctccct ttggccgctc gggaacccc                                     29

<210> SEQ ID NO 29
<211> LENGTH: 26
<212> TYPE: DNA
<213> ORGANISM: Artificial Sequence
<220> FEATURE:
<223> OTHER INFORMATION: forward primer sequence FW5 used to amplify a
      gene cassette containing ~200 bp upstream of UPF1, the Kan-MX6,
      and ~200 bp downstream of UPF1

<400> SEQUENCE: 29
aatgaaaagc ttaccagaaa cttacg                                        26

<210> SEQ ID NO 30
<211> LENGTH: 23
<212> TYPE: DNA
<213> ORGANISM: Artificial Sequence
<220> FEATURE:
```

```
<223> OTHER INFORMATION: reverse primer sequence FW6 used to amplify a
      gene cassette containing ~200 bp upstream of UPF1, the Kan-MX6,
      and ~200 bp downstream of UPF1

<400> SEQUENCE: 30
ggctaggata tcaagtccat gcc                                              23

<210> SEQ ID NO 31
<211> LENGTH: 26
<212> TYPE: DNA
<213> ORGANISM: Artificial Sequence
<220> FEATURE:
<223> OTHER INFORMATION: forward primer sequence used to amplify genomic
      DNA ~300 bp away from the UPF1 gene

<400> SEQUENCE: 31
gatttgggag ggacaccttt atacgc                                           26

<210> SEQ ID NO 32
<211> LENGTH: 25
<212> TYPE: DNA
<213> ORGANISM: Artificial Sequence
<220> FEATURE:
<223> OTHER INFORMATION: reverse primer sequence used to amplify genomic
      DNA ~300 bp away from the UPF1 gene

<400> SEQUENCE: 32
ttcattagaa gtacaatggt agccc                                            25

<210> SEQ ID NO 33
<211> LENGTH: 85
<212> TYPE: DNA
<213> ORGANISM: E. coli

<400> SEQUENCE: 33
ggtggggttc ccgagcggcc aaagggagca gactctaaat ctgccgtcat cgacttcgaa      60
ggttcgaatc cttcccccac cacca                                            85

<210> SEQ ID NO 34
<211> LENGTH: 87
<212> TYPE: DNA
<213> ORGANISM: E. coli

<400> SEQUENCE: 34
gcccggatgg tggaatcggt agacacaagg gattctaaat ccctcggcgt tcgcgctgtg      60
cgggttcaag tcccgctccg ggtacca                                          87
```

The invention claimed is:

1. A method of expressing a prokaryotic tRNA in a eukaryotic cell, comprising:
   transducing the eukaryotic cell with a nucleic acid molecule encoding an external RNA polymerase III promoter (pol III) operably linked to a nucleic acid molecule encoding the prokaryotic tRNA,
   thereby expressing the prokaryotic tRNA in the eukaryotic cell.

2. The method of claim 1, wherein the eukaryotic cell is a mammalian cell or a yeast cell.

3. The method of claim 1, wherein the cell is substantially Nonsense-Mediated mRNA Decay—(NMD)-deficient.

4. The method of claim 1, wherein the pol III promoter is a type-3 pol III promoter or an internal leader promoter.

5. The method of claim 1, wherein the prokaryotic tRNA is an *E. coli* tRNA.

6. The method of claim 1, wherein the prokaryotic tRNA is a suppressor tRNA.

7. The method of claim 1, further comprising transducing the eukaryotic cell with a nucleic acid molecule that encodes an aminoacyl-tRNA synthetase operably linked to a promoter.

8. The method of claim 7, wherein the aminoacyl-tRNA synthetase is specific for an unnatural amino acid, and wherein the method is a method of co-expressing the prokaryotic tRNA and the unnatural amino acid.

9. The method of claim 7, wherein the tRNA and the aminoacyl-tRNA synthetase form an orthogonal pair.

10. The method of claim 1, wherein the nucleic acid encoding the pol III promoter operably linked to the nucleic acid encoding the prokaryotic tRNA further comprises either a 3'-CCA trinucleotide at a 3'-end of the nucleic acid encoding the prokaryotic tRNA or a 3' flanking nucleic acid sequence at the 3' end of the nucleic acid encoding the prokaryotic tRNA.

11. A kit comprising:
a vector comprising a nucleic acid molecule encoding an external pol III promoter operably linked to a nucleic acid molecule that encodes a prokaryotic tRNA.

12. The kit of claim 11, wherein the vector is an expression plasmid.

13. The kit of claim 11, wherein the pol III promoter is a type-3 pol III promoter or an internal leader promoter.

14. The kit of claim 11, wherein the prokaryotic tRNA is an *E. coli* tRNA.

15. The kit of claim 11, wherein the prokaryotic tRNA is a suppressor tRNA.

16. The kit of claim 12, wherein the plasmid further comprises a nucleic acid molecule that encodes an aminoacyl-tRNA synthetase.

17. The kit of claim 16, wherein the aminoacyl-tRNA synthetase is specific for an unnatural amino acid.

18. The kit of claim 16, wherein the tRNA and the aminoacyl-tRNA synthetase form an orthogonal pair.

19. The kit of claim 11, further comprising
   (a) a reporter vector, wherein the reporter vector comprises a promoter operably linked to a nucleic acid sequence encoding a detectable product, and/or
   (b) a yeast cell that is substantially NMD-deficient.

20. A stable eukaryotic cell line expressing a nucleic acid molecule encoding an external pol III promoter operably linked to a prokaryotic tRNA.

21. The stable cell line of claim 20, wherein the cell line is a mammalian cell line or a yeast cell line.

22. The cell line of claim 20, wherein the cell line is substantially Nonsense-Mediated mRNA Decay—(NMD)-deficient.

23. The stable cell line of claim 20, wherein the pol III promoter is a type-3 pol III promoter or an internal leader promoter.

24. The stable cell line of claim 20, wherein the prokaryotic tRNA is an *E. coli* tRNA.

25. The stable cell line of claim 20, wherein the prokaryotic tRNA is a suppressor tRNA.

26. The stable cell line of claim 20, wherein stable cell line further expresses an aminoacyl-tRNA synthetase.

27. The stable cell line of claim 26, wherein the aminoacyl-tRNA synthetase is specific for an unnatural amino acid.

28. The stable cell line of claim 26, wherein the tRNA and the aminoacyl-tRNA synthetase form an orthogonal pair.

\* \* \* \* \*